(12) United States Patent
Kim et al.

(10) Patent No.: US 9,878,328 B2
(45) Date of Patent: Jan. 30, 2018

(54) APPARATUS AND METHOD FOR MULTIPLE REACTIONS IN SMALL VOLUMES

(75) Inventors: Namyong Kim, Palo Alto, CA (US); Siah Chong Cheong, Singapore (SG); Melvin Han Wen Lye, Singapore (SG); Mark Siew Peng Phong, Singapore (SG); Li Li, Singapore (SG); Teow Soon Seah, Singapore (SG)

(73) Assignee: Curiox Biosystems Pte Ltd., Singapore (SG)

( * ) Notice: Subject to any disclaimer, the term of this patent is extended or adjusted under 35 U.S.C. 154(b) by 0 days.

(21) Appl. No.: 13/811,638

(22) PCT Filed: Jul. 25, 2011

(86) PCT No.: PCT/SG2011/000263
§ 371 (c)(1),
(2), (4) Date: Jan. 22, 2013

(87) PCT Pub. No.: WO2012/011877
PCT Pub. Date: Jan. 26, 2012

(65) Prior Publication Data
US 2013/0123139 A1    May 16, 2013

Related U.S. Application Data

(60) Provisional application No. 61/367,049, filed on Jul. 23, 2010.

(51) Int. Cl.
*B01L 3/00* (2006.01)
*C12M 1/00* (2006.01)
*C12M 1/32* (2006.01)

(52) U.S. Cl.
CPC ......... *B01L 3/5085* (2013.01); *B01L 3/50853* (2013.01); *C12M 23/12* (2013.01);
(Continued)

(58) Field of Classification Search
CPC ............... B01L 3/5085; B01L 3/50855; B01L 2300/06187; B01L 2300/0829; B01L 2200/0689; C12M 23/12
(Continued)

(56) References Cited

U.S. PATENT DOCUMENTS 3,426,108 A   2/1969 Britten
3,754,872 A   8/1973 Zauft
(Continued)

FOREIGN PATENT DOCUMENTS

CN   1460723   12/2003
CN   1858593   11/2006
(Continued)

OTHER PUBLICATIONS

Agency for Science, Technology and Research, Notification of First Office Action, CN 201110401674.9, Dec. 30, 2013, 9 pgs.
(Continued)

*Primary Examiner* — Karla A Dines
(74) *Attorney, Agent, or Firm* — Morgan, Lewis & Bockius LLP

(57) ABSTRACT

This describes an apparatus comprising a plate with a number of elements having a hydrophilic surface arranged in an array with an overlay having a hydrophobic surface. A height of the overlay is between about 5% and 100% of the diameter of the elements. The application also discloses a wall circumferential to the plate; and a removable grid insertable into the apparatus, said grid comprising dividers enclosing a number of through-holes, said through-holes spaced in the grid to allow alignment of the through-holes of the grid over the elements in the plate when said grid is inserted into the apparatus, said dividers of the grid inserted into the apparatus form sides of wells bottomed by the plate and at least one element on said plate.

30 Claims, 13 Drawing Sheets

(52) U.S. Cl.
CPC .......... *C12M 23/34* (2013.01); *B01L 3/50855* (2013.01); *B01L 2200/0689* (2013.01); *B01L 2300/0618* (2013.01); *B01L 2300/0829* (2013.01)

(58) Field of Classification Search
USPC ......................................................... 506/9
See application file for complete search history.

(56) References Cited

U.S. PATENT DOCUMENTS

| | | |
|---|---|---|
| 5,041,266 A | 8/1991 | Fox |
| 5,219,528 A | 6/1993 | Clark |
| 5,229,163 A | 7/1993 | Fox |
| 5,506,121 A | 4/1996 | Skerra et al. |
| 5,560,811 A | 10/1996 | Briggs et al. |
| 5,691,147 A | 11/1997 | Draetta et al. |
| RE35,894 E | 9/1998 | Ellison et al. |
| 5,817,510 A | 10/1998 | Pandey et al. |
| 6,048,908 A | 4/2000 | Kitagawa |
| 6,086,825 A | 7/2000 | Sundberg et al. |
| 6,103,493 A | 8/2000 | Skerra et al. |
| 6,130,098 A | 10/2000 | Handique et al. |
| 6,238,626 B1 | 5/2001 | Higuchi et al. |
| 6,331,441 B1 | 12/2001 | Balch et al. |
| 6,534,014 B1 | 3/2003 | Mainquist et al. |
| 6,565,813 B1 | 5/2003 | Garyantes |
| 6,578,952 B1 | 6/2003 | Sugiyama et al. |
| 6,664,044 B1 | 12/2003 | Sato |
| 6,699,437 B1 | 3/2004 | Astle |
| 6,716,629 B2 | 4/2004 | Hess et al. |
| 6,767,733 B1* | 7/2004 | Green .................... B01L 3/502 422/82.11 |
| 6,902,705 B1 | 6/2005 | Caillat et al. |
| 7,163,823 B2 | 1/2007 | Patno et al. |
| 7,344,877 B1 | 3/2008 | Camacho et al. |
| 7,439,056 B2* | 10/2008 | Duffy et al. ............... 435/288.4 |
| 7,666,362 B2 | 2/2010 | Shanler |
| 7,794,799 B1* | 9/2010 | Kim .................... B01J 19/0046 427/2.11 |
| 7,854,343 B2 | 12/2010 | Ellson et al. |
| 8,221,697 B2 | 7/2012 | Nichols et al. |
| 8,987,174 B2 | 3/2015 | Routenberg |
| 2002/0016009 A1 | 2/2002 | Ogura |
| 2002/0064482 A1 | 5/2002 | Tisone et al. |
| 2002/0094533 A1* | 7/2002 | Hess .................... B01J 19/0046 435/6.14 |
| 2003/0032046 A1 | 2/2003 | Duffy et al. |
| 2003/0083474 A1 | 5/2003 | Schmidt |
| 2003/0113813 A1 | 6/2003 | Heidaran et al. |
| 2003/0124599 A1 | 7/2003 | Chen et al. |
| 2003/0148401 A1* | 8/2003 | Agrawal ............ B01J 19/0046 506/9 |
| 2003/0209560 A1 | 11/2003 | Hui et al. |
| 2004/0106156 A1 | 6/2004 | Perez et al. |
| 2004/0106191 A1 | 6/2004 | Muser |
| 2004/0136876 A1 | 7/2004 | Fouillet et al. |
| 2004/0142460 A1 | 7/2004 | Cima et al. |
| 2004/0208792 A1 | 10/2004 | Linton et al. |
| 2004/0234966 A1 | 11/2004 | Bryning et al. |
| 2005/0045539 A1 | 3/2005 | Yu et al. |
| 2005/0079105 A1 | 4/2005 | Hunter et al. |
| 2005/0084423 A1 | 4/2005 | Zarowitz et al. |
| 2005/0186579 A1* | 8/2005 | Dellinger ............ C12Q 1/6834 435/5 |
| 2006/0013031 A1 | 1/2006 | Ravkin et al. |
| 2006/0051249 A1 | 3/2006 | Knebel et al. |
| 2006/0078893 A1 | 4/2006 | Griffiths et al. |
| 2006/0105453 A1 | 5/2006 | Brenan et al. |
| 2006/0105462 A1 | 5/2006 | Sellek-Prince |
| 2006/0142468 A1 | 6/2006 | Downing, Jr. et al. |
| 2006/0142564 A1 | 6/2006 | Gyollai et al. |
| 2007/0003448 A1 | 1/2007 | Kanigan et al. |
| 2007/0005169 A1 | 1/2007 | Rohnert et al. |
| 2007/0077651 A1 | 4/2007 | Guarino et al. |
| 2007/0099208 A1 | 5/2007 | Drmanac |
| 2007/0117765 A1 | 5/2007 | Sauve et al. |
| 2008/0003670 A1* | 1/2008 | Martin et al. .............. 435/297.5 |
| 2008/0003671 A1 | 1/2008 | Martin |
| 2008/0173544 A1* | 7/2008 | Seul .................. B01L 3/502715 204/478 |
| 2009/0142564 A1 | 6/2009 | Plissonnier et al. |
| 2009/0148348 A1 | 6/2009 | Pettigrew et al. |
| 2009/0227474 A1 | 9/2009 | Gordon et al. |
| 2009/0286317 A1* | 11/2009 | Demmler ............... C12M 23/12 435/377 |
| 2010/0000304 A1 | 1/2010 | Kim et al. |
| 2010/0167950 A1 | 7/2010 | Juang et al. |
| 2010/0297767 A1* | 11/2010 | Hattori ................ C12N 5/0606 435/395 |
| 2012/0220497 A1 | 8/2012 | Jacobson |

FOREIGN PATENT DOCUMENTS

| | | | |
|---|---|---|---|
| CN | 101031363 | 9/2007 | |
| DE | 10043042 C2 | 6/2002 | |
| EP | 0812693 A1 | 12/1997 | |
| EP | 1348533 B1 | 7/2002 | |
| EP | 1358939 A2 | 4/2003 | |
| EP | 1316360 B1 | 6/2003 | |
| EP | 1386657 A1 | 7/2003 | |
| EP | 1473079 A1 | 2/2004 | |
| EP | 1788047 A1 | 8/2005 | |
| EP | 1683571 A1 | 1/2006 | |
| EP | 1399263 B1 * | 8/2009 | .......... B01L 3/50851 |
| GB | 1291610 | 10/1972 | |
| GB | 2332273 A | 6/1999 | |
| GB | 2334954 A | 9/1999 | |
| JP | 3120453 B2 | 12/2000 | |
| JP | 2002-502955 A | 1/2002 | |
| JP | 2003-033177 A | 2/2003 | |
| JP | 2004-020280 A | 1/2004 | |
| JP | 2004-077476 A | 3/2004 | |
| JP | 2004-535176 A | 11/2004 | |
| JP | 2005-003803 A | 1/2005 | |
| JP | 2005-099004 A | 4/2005 | |
| WO | WO 1996-23879 | 8/1996 | |
| WO | WO 1998-055852 | 12/1998 | |
| WO | WO99/39829 A1 | 8/1999 | |
| WO | WO99/55826 A1 | 11/1999 | |
| WO | WO 2000-014311 | 3/2000 | |
| WO | WO 00-58735 | 10/2000 | |
| WO | WO 2001-004144 A2 | 1/2001 | |
| WO | WO 2003-029462 A1 | 4/2003 | |
| WO | WO 2004-030820 A2 | 4/2004 | |
| WO | WO 2004-111610 A2 | 12/2004 | |
| WO | WO 2005/019254 A1 | 3/2005 | |
| WO | WO 2005/019255 A1 | 3/2005 | |
| WO | WO 2005/019256 A2 | 3/2005 | |
| WO | WO 2006/004739 A2 | 1/2006 | |
| WO | WO 2006/046699 A1 | 5/2006 | |
| WO | WO 2007/102785 A1 | 9/2007 | |
| WO | WO2008/063136 A1 | 5/2008 | |
| WO | WO 98/47003 | 10/2008 | |
| WO | WO 2010/120249 A1 | 10/2010 | |
| WO | WO 2012/011877 A2 | 1/2012 | |

OTHER PUBLICATIONS

Curiox Biosystems Pte Ltd, International Search Report and Written Opinion, PCT/SG201-1/000263, dated Feb. 29, 2012, 20 pgs.

Curiox Biosystems Pte Ltd, International Preliminary Report on Patentability, PCT/SG2011/000263, Dec. 21, 2012, 5 pgs.

Kanta, Preparation of Silica-on-Titania Patterns with a Wettability Contrast, American Chemical Society, Dec. 21, 2004, 5 pgs.

Agency for Science, Technolgy and Research, International Preliminary Report on Patentability, PCT/SG2007/000393, dated May 26, 2009, 4 pgs.

Agency for Science, Technolgy and Research, International Search Report and Written Opinion of the ISA, PCT/SG2007/000393, dated Feb. 20, 2008, 7 pgs.

(56) References Cited

OTHER PUBLICATIONS

Agency for Science, Technolgy and Research, Notification of Reasons for Refusal, JP 2009-538373, dated Nov. 10, 2011, 7 pgs.
Agency for Science, Technolgy and Research, Notification of Reasons for Refusal, JP 2012-196318, dated Dec. 10, 2013, 3 pgs.
Agency for Science, Technolgy and Research, Notification of the First Office Action, CN 200780048922.8, dated Nov. 12, 2010, 4 pgs (available in Chinese only).
Agency for Science, Technolgy and Research, Notification of the Second Office Action, CN 200780048922.8, dated May 17, 2011, 4 pgs.
Agency for Science, Technolgy and Research, Notification on the Grant of Patent Right for Invention, CN 200780048922.8, dated Sep. 22, 2011, 1 pg.
Agency for Science, Technolgy and Research, Supplementary Search Report, EP 07835548.4, dated Jun. 30, 2010, 5 pgs.
Asberg. Surgace Energy Modified Chips for Detection of Conformational States and Enzymatic Activity in Biomolecules, Langmuir, 2006, pp. 2205-2211.
Beck, Improving Stamps for 10 nm Level Wafer Scale Nanoimprint Lithography, Microelectron. Eng., 2002, pp. 61-62 and 441.
Benor, Microstructuring by Microcontact Printing and Selective Surface Dewetting, J. of Vacuum Science & Technology B, 2007, pp. 1321-1326.
Beste, Small Antibody-like Proteins with Prescrived Ligand Specificities Derived from the Lipocalin Fold, Proc. Natl. Acad. Sci, USA, 1999, pp. 1898-1903.
Biffinger, The Polar Hydrophobicity of Cluorinated Compounds, ChemBioChem, 2004, pp. 622-627.
Burbulis, Quantifying Small Numbers of Antibodies with a 'Near-Universal' Protein-DNA Chimera, Nature Methods, 2007.
Chiriac, Magnetic GMI Sensor for Detection of Biomolecules, J. Magnetism and Magnetic Materials, 2005, pp. 671-676.
Churaev, Wetting of Low-Energy Surgfaces, Advances in Colloid and Interface Science, 2007, pp. 134-135, 15-23.
Curiox Biosystems Pte Ltd, International Preliminary Report on Patentability, PCT/SG2010/000153, dated Oct. 18, 2011, 15 pgs.
Curiox Biosystems Pte Ltd, International Search Report and Written Opinion, PCT/IB2013/000623, dated Jul. 10, 2013, 7 pgs.
Curiox Biosystems Pte Ltd, International Search Report and Written Opinion, PCT/SG2006/000050, dated May 8, 2006, 21 pgs.
Curiox Biosystems Pte Ltd, International Search Report and Written Opinion, PCT/SG2010/000153, dated Sep. 17, 2010, 20 pgs.
Daniel, Vibration-Actuated Drop Motion on Surfaces bor Batch Microfluidic Processes, Langmuir, 2005, pp. 4220-4228.
Dill, Modeling Water, The Hydrophobic Effect and Ion Solvation, Annu. Rev. Biophys. Biomol. Struc, 2005, pp. 173-199.
Gao, A Commercially Available Perfectly Hydrophobic Material, Langmuir, 2007, pp. 9125-9127.
Gascoyne, Dielectrophoresis-based Programmable Fluidic Processors, Lab-on-a-Chip, 2004, pp, 299-309.
Genua, Functional Patterns Obtained by Nanoimprinting Lithography and Subsequent Growth of Polymer Brushes, Nanotechnology, 2007, 215301, 7 pgs.
Gill, Pharmaceutical Drug Discovery Using Novel Protein Scaffolds, Current Opinion in Biotechnology, 2006, 653-658.
Giovambattista, Effect of Surface Polarity on Water Contact Angle and Interfacial Hydration Structure, J. Phys. Chem., 2007, pp. 9581-9587.
Goddard, Polymer Surface Modification for the Attachment of Bioactive Compounds, Progress in Polymer Science, 2007, pp. 698-725.
Griffiths, Miniaturising the Laboratory in Emulsion Droplets, Trends in Biotechnology, 2006, pp. 395-402.
Herrmann, Enxymatically-Generated Fluorescent Detection in Micro-Channels with Internal Magnetic Mixing for the Development of Parallel Miicrofluidic ELISA, Lab-on-a-Chip, 2006, pp. 555-560.
Holt, Domain Antibodies: Proteins for Therapy, Trends Biotechnol, 2003, pp. 484-490.
Hutten, New Magnetic Nanoparticles for Biotechnology, J. Biotech., 2004, pp. 47-63.
Iliades, Triabodies: Single Chain Fv Fragments without a Linker Form Trivalent Trimers, FEBS Lett, 1997, pp. 437-441.
Jakobs, Micrometer Scale Gel Patterns, Colloids & Surfaces A: PhysioChem. Eng. Aspects, 2006, pp. 33-40.
Jung, Wetting Transition of Water Droplets on Superhydrophobic Patterned Surfaces, Scripta Materialia, 2007, pp. 1057-1060.
Kim, Final Office Action, U.S. Appl. No. 13/264,913, dated Jun. 21, 2013, 11 pgs.
Kim, Notice of Allowance, U.S. Appl. No. 12/282,162, dated May 14, 2012, 7 pgs.
Kim, Office Action, U.S. Appl. No. 12/282,162, dated Jun. 27, 2011, 8 pgs.
Kim, Office Action, U.S. Appl. No. 13/264,913, dated Nov. 7, 2012, 9 pgs.
Kim, Office Action, U.S. Appl. No. 13/264,913, dated Sep. 26, 2013, 10 pgs.
Kusumaatmaja, Controlling Drop Size and Polydispersity Using Chemically Patterned Surfaces, Langmuir, 2007, pp. 956-959.
Kwon, Quantitative Evaluation of the Relative Cell Permeability of Peptoids and Peptides, J. AM. Chem. Soc., 2007, pp. 1508-1509.
Leek, Final Office Action, U.S. Appl. No. 11/984,197, dated May 8, 2012, 10 pgs.
Leek, Office Action, U.S. Appl. No. 11/984,197, dated Mar. 14, 2013, 11 pgs.
Leek, Office Action, U.S. Appl. No. 11/984,197, dated May 26, 2011, 11 pgs.
Leek, Office Action, U.S. Appl. No. 11/984,197, dated Jul. 31, 2013, 12 pgs.
Li, What Do We Need for a Superhydrophobic surface? A review on the recent progress in the preparation of superhydrophobic surfaces, Chem. Soc. Rev, 2007, pp. 1350-1368.
Luca, Preparation of TIOx Thin Films by Reactive Pulsed-Laser Ablation, J. Optoelectronics and Adv. Materials, Apr. 2005, pp. 625-630.
Lundgren, Modeling of Wetting: A Study of Nanowetting at Rough and Heterogeneous Surfaces, Langmuir, 2007, pp. 1187-1194.
Ma, Superhydrophobic Surfaces, Current Opinion in Colloid & Interface Science, 2006, pp. 193-202.
Mardare, Microelectrochemical Lithography: A method for Direct Writing of Surface Oxides, Electrochimica Acta, 2007, pp. 7865-7869.
Matsuda, Phosphorylcholine-Endcapped Oligomer and Block Co-Oligomer and Surface Biological Reactivity, Biomaterials, 2003, pp 4517-4527.
Meyer, Recent Progress in Understanding Hydrophobic Interactions, Proc. Netl. Acad. Sci USA, 2006, pp. 15739-15746.
Mosavi, The Ankyrin Repeat as Molecular Architecture for Protein Recognition, Protein Science, 2004, pp. 1435-1448.
Opdahl, Polymer Surface Science, The Chemical Record, 2001, pp. 101-122.
Perfulorodecalin-FluoroMed, http://fluoromed.com/products/perfluorodecalin.html (no date).
Pollack, Electrowetting-based Actuation of Liquid Droplets for Microfluidic Applications, Appl. Phys. Lett., 2000, pp. 1725-1726.
Popp, Sortagging: A versatile Method for Protein Labeling, Nature Chemical Biology, 2007, pp. 707-708.
Rastogi, Development and Evaluation of Realistic Microbioassys in Freely Suspended Droplets on a Chip, Biomicrofludics, 2007, 014107-1-014107-17.
Roach, Controllling Nonspecific Protein Adsorption in a Plug-Based Microfluidic System by Controlling Interfacial Chemistry Using Fluorous-Phase Surfactants, Analytical Chemistry, vol. 77, No. 3, Feb. 1, 2005, pp. 785-796.
Ronaghi, Pyrosequestering Sheds Light on DNA Sequestering, Genome Research, 2001, pp. 3-11.
Rose, Microdispensing Technologies in Drug Discovery, Drug Discovery Today, 1999, pp. 411-419.
Satriano, Bacterial Adhesion Onto Nanopatterned Polymer Surfaces, Materials Science & Engineering C, 2006, pp. 942-946.

(56) References Cited

OTHER PUBLICATIONS

Silverman, Multivalent Avimer Proteins Evolved by Exon Shuffling of a Family of Human Receptor Domains, Nature Biotechnology, 2005, pp. 1556-1561.
Skerra, Engineered Protein Scaffolds for Molecular Recognition, J. Mol. Recognit., 2000, pp. 167-187.
Song, Miniature Biochip System for Detection of *Sscherichi coli* O157:H7 Based on Antibody-Immobilized Capillary Reactors and Enzyme-linked Immunosorbent Assay, Analytica Chimica Acta, 2004, pp. 115-121.
Stephenson, Quantifying the Hydrophobic Effect: A Computer Simulation-Molecular-Thermodynamic Model for the Self-Assembly of Hydrophibic and Amphiphilic Solutes in Aqueous Solution, Jp. Phys. Chem. B, 2007, 1025-1044.
Stone, The Assembly of Single Domain Antibodies into Bispecific Decavalent Molecules, J. Immunological Methods, 2007, pp. 88-94.
Sundberg, Contact Angle Measurements by Confocal Microscopy for Non-Destructive Microscale Surface Characterization, J. Colloid and Interface Science, 2007, pp. 454-460.
Van Oss, Long-Rage and Short-Range Mechanisms of Hydrophobic Attraction and Hydrophilic Repulsion in Specific and Aspecific Interactions, J. Mol. Recognit., 2003, pp. 177-190.
Wang, Flow-Focusing Generation of Monodisperse Water Droplets Wrapped by Ionic Liquid on Microfiuidic Chips: From Plug to Sphere, langmuir, 2007, pp. 11924-11931.
Wang, In-Situ Wilhelmy Balance Surface Energy Determination of Poly(3-hexylthiophere) and Poly(3,4-ethylenedioxythiophere) during Electrochemical Doping-Dedoping, Langmuir, 2006, pp. 9287-9294.
Washizu, Elecrostatic Actuation of Liquid Droplets for Microreactor Applications, IEEE Transactions on Industry Applications, vol. 34, No. 4, Jul.-Aug. 1998.
West, Microplasma Writing for Surface-Directed Millifludics, Lab-on-a-Chip, 2007, pp. 981-983.
Widom, The Hydrophobic Effect, Phys. Chem. Chem. Phys., 2003, pp. 3085-3093.
Wixforth, Flatland Fluidics, mstnews, 2002, pp. 42-43.
Curiox Biosystems Pte Ltd, International Preliminary Report on Patentablity, PCT/IB2013/000623, dated Aug. 5, 2014, 7 pgs.
Agency for Science, Technology and Research, Communication Pursuant to Article 94, EP07835548-4, dated Jul. 17, 2015, 3 pgs.
Curiox Biosystems PTE Ltd., International Search Report and Written Opinion, PCT/US2015/019760, dated Jun. 2, 2015, 12 pgs.
Curiox Biosystems Pte Ltd, International Search Report and Written Opinion, PCT/US2015/019760, dated Jun. 2, 2015, 12 pgs.
Kim, Office Action, U.S. Appl. No. 14/326,780, dated Oct. 28, 2015, 13 pgs.
Kim, Office Action, U.S. Appl. No. 14/452,172, dated Oct. 23, 2015, 16 pgs.
Kim, Office Action, U.S. Appl. No. 14/338,168, dated Nov. 6, 2015, 8 pgs.
Agency for Science, Technology and Research, First Examination Report, IN3674/CHEN/P2009, dated Oct. 10, 2016, 9 pgs.
Leek, Notice of Allowance, U.S. Appl. No. 14/246,004, dated Sep. 15, 2016, 8 pgs.
Cheng, Office Action, U.S. Appl. No. 14/050,321, dated Feb. 26, 2016, 31 pgs.
Erfle et al., "Reverse Transfections on Cell Arrays for High Content Screening Microscopy," Nature Protocols, Mar. 1, 2007, vol. 2 No. 2, 8 pgs.
Lowe et al., "Perfluorochemicals: Their Applications and Benefits to Cell Culture," Tibtech, Jun. 1998, vol. 16, 6 pgs.
Takahashi et al., Induction of Pluripotent Stem Cells from Mouse Embryonic and Adult Fibroblast Cultures by Defined Factors, Cell, Aug. 25, 2006, 126, 14 pgs.
Vancha et al., "Use of Polyethyleneimine Polymer in Cell Culture as Attachment Factor and Lipofection Enhancer," BMC Biotechnology, Oct. 15, 2004, 12 pgs.
Kim, Final Office Action, U.S. Appl. No. 14/326,780, dated May 10, 2016, 11 pgs.
Kim, Notice of Allowance, U.S. Appl. No. 14/326,780, dated Sep. 22, 2016, 7 pgs.
Kim, Final Office Action, U.S. Appl. No. 14/452,172, dated Jun. 3, 2016, 17 pgs.
Kim, Office Action, U.S. Appl. No. 14/338,168, dated Jun. 22, 2016, 9 pgs.
Curiox Biosystems Pte Ltd, International Search Report and Written Opinion, PCT/SG2006/000050, dated May 8, 2006, 6 pgs.
Perfluorodecalin-FluoroMed, downloaded on Sep. 5, 2013, from http://fluoromed.com/products/perfluorodecalin.html, 1 pg.
Cheng, Office Action, U.S. Appl. No. 14/050,321, dated Mar. 31, 2017, 38 pgs.
Kim, Notice of Allowance, U.S. Appl. No. 14/338,168, dated Sep. 13, 2017, 8 pgs.
Leek, Office Action, U.S. Appl. No. 15/424,604, dated Aug. 11, 2017, 7 pgs.

\* cited by examiner

Unwashed well

After 1st wash

After 2nd wash

After 6th wash

APPARATUS AND METHOD FOR MULTIPLE REACTIONS IN SMALL VOLUMES

CROSS REFERENCE TO RELATED APPLICATIONS

This application is a United States National Stage Application filed under 35 U.S.C. § 371 of PCT Patent Application Serial No. PCT/SG2011/000263 filed on Jul. 25, 2011, which claims priority from U.S. provisional patent application No. 61/367,049, filed Jul. 23, 2010, entitled, "Improved Handling and Use of Patterned Fluidic Array," the disclosure of which is incorporated herein, it its entirety, by reference.

BACKGROUND OF THE INVENTION

The invention generally relates generally to the fields of biology, chemistry, and biochemistry and, more particularly, to devices and methods for performing multiple biological, biochemical, and chemical assays in small volumes.

In the fields of biology, chemistry, and biochemistry, often subtle changes to a molecule or a cell in a reaction can have consequences on the results of reactions or assays using that molecule or cell. For example, changing a single amino acid (e.g., an alanine to a serine) in a polypeptide molecule or changing the growth conditions of a cell (e.g., growth in the presence of 10% fetal bovine serum versus 5% fetal bovine serum) can affect how the polypeptide or cell responds in a given reaction (e.g., whether or not the polypeptide binds to a specific binding agent or whether the cell responds to a growth factor).

Microtiter plates have been used for decades to enable the multiple reactions in small volume for applications including high-throughput screening. For example, one commonly used immunological assay, the Enzyme-linked immunosorbent assay or "ELISA" can be used to determine if a member of a binding agent/ligand pair is present in a sample, and, if present, how much is present. For example, one member of the binding agent/ligand pair (e.g., an antibody) can be immobilized to the bottom of the multiple wells on a microtiter plate (e.g., through non-specific adsorption of the antibody into the wells of the plate), and then multiple samples can be assessed as to the presence and/or concentration of the antibody's specific ligand by adding each different sample to one of the wells of the microtiter plate and then detecting binding of the sample to the well (e.g., using a detectably labeled antibody specific for the ligand).

Standard microtiter plates are commercially available from numerous manufacturers (e.g., Thermo Fisher Scientific, Waltham, Mass.) and can be made from numerous different materials (see, e.g., Bouche, F B et al., Clinical Chemistry 48: 378, 380, 2002). However, standard microtiter plates have several limitations. Most relevantly, they are limited by the number of wells on the plate. To increase the number of reactions that can be run (e.g., increase the number of samples that can be tested at the same time), the number of wells on a single plate can vary from 6 wells to 1536 wells per plate.

Recently, in the field of biology and biochemistry, DNA microarrays and protein microarrays have been employed to increase still further the number of different reactions that can be performed simultaneously. DNA microarrays are made by adhering DNA probes (e.g., single-stranded probes) to the surface of a chip or slide (e.g., made of glass or silicon) in an array of dots or spots. Different samples of DNA are then added to each of the spots and screened for the ability to bind the spots (e.g., through hybridization of a nucleic acid in the sample to the surface-bound probe). Detection of binding can then be made, for example, by fluorescent or chemical means (which, in some cases, is preceded by amplification of the bound nucleic acid molecules to enhance detection). DNA microarray technology is well known (see, e.g., U.S. Pat. Nos. 5,700,637; 7,323,555; 6,862,363; 7,414,117; and 7,359,537).

Of course there are some fundamental differences between microarrays and microtiter plates. In microtiter plates, a reaction in an individual well can be carried out independently regardless of a reaction in the neighboring wells. In contrast, the active spots (similar to 'wells' of a microtiter plate) in microarrays are usually exposed to a common solution. Unlike micrrotiter plates, microarrays do not offer any capability where an individual spot can be exposed to a different solution during a repeated process of addition, incubation, and washing.

Protein arrays on glass slides have also been described (see Arenkov et al., Anal. Biochem 278: 123-131, 2000; Guschin et al., Anal. Biochem. 250: 202-211, 1997; MacBeath and Schreiber, Science 289: 1760-1763, 2000) as well as protein arrays on microwell or nanowell chips (see Zhu and Snyder, Curr. Opin. Chem. Biol. 5(1):40-45, 2001). However, in addition to having the same limitations as DNA microarrays, protein arrays have additional challenged. For example, complex chemicals, such as proteins and other non-nucleic acid biological molecules (e.g., fatty acids and carbohydrates), are more difficult to use in microarrays for multiple reactions. This is due a variety of actors including, for example, the storage and binding requirements of the molecules (e.g., storage may be preferable at $-20°$ C. while binding may be preferable at $37°$ C. For these reasons, protein microarrays are generally less specific than assays such as ELISAs that use microtiter plates.

Accordingly, there is a need find a solution for running multiple reactions that can combine the specificity of microtiter plate assays with the microarray's increased number of reactions that can be in multiple.

BRIEF SUMMARY OF THE INVENTION

The various embodiments of the invention are based on the discovery of a system that combines the advantages of a standard microtiter plate with the advantages of a flat microarray. The various aspect of the invention, thus, facilitates multiple reactions (e.g., involving molecules and/or living cells) in small volumes.

Accordingly, in a first aspect, the invention provides a system comprising: an apparatus comprising: a plate comprising a number of elements having a first surface energy arranged in an array with an overlay having a second surface energy, and a wall circumferential to the plate; and a removable grid insertable into the apparatus to be positioned over the plate and within the wall of the apparatus, said grid comprising dividers enclosing a number of through-holes, said through-holes spaced in the grid to allow alignment of the through-holes of the grid over the elements in the plate when said grid is inserted into the apparatus, wherein said dividers of the grid inserted into the apparatus form sides of wells bottomed by the plate and at least one element on said plate.

In another aspect, the invention provides a removable grid insertable into an apparatus comprising a plate comprising a number of elements having a first surface energy arranged in an array with an overlay having a second surface energy and a wall circumferential to the plate, said grid comprising dividers enclosing a number of through-holes, said through-holes spaced in the grid to allow alignment of the through-holes of the grid over the elements in the plate when said grid is inserted into the apparatus, wherein said dividers of the grid inserted into the apparatus form sides of wells bottomed by the plate and at least one element on said plate.

In some embodiments, the apparatus further comprises a positioning structure adjacent to the interior of the wall so as to guide alignment of the through-holes of the grid over the elements when the grid is inserted into the apparatus. In various embodiments, the number of through-holes in the grid is the same as or is smaller than the number of elements in the plate. In some embodiments, each through-hole is aligned over a single element in the plate. In some embodiments, each through-hole is aligned over multiple elements in the plate.

In some embodiments, the first surface energy results in a hydrophilic surface. In some embodiments, the second surface energy results in a hydrophobic surface. In some embodiments, the grid has a second surface energy.

In further embodiments, the grid further comprises offsetting features on the surface of the grid that touches the plate when the grid is inserted into the apparatus. In some embodiments, the grid further comprises at least one structure on the surface of the grid that does not touch the plate when the grid is inserted into the apparatus, said structure sized for a user (e.g., a human or an automated device) to grab the grid and insert or remove the grid from the apparatus. In some embodiments, the grid further comprises a reservoir encompassing at least one through-hole of the grid, said reservoir on the surface of the grid that does not touch the plate when the grid is inserted into the apparatus.

In various embodiments, the dividers of the grid and the wall of the apparatus are of the same height. In some embodiments, the dividers of the grid are of a height that is higher than the height of the wall of the apparatus.

In various embodiments, the grid further comprises a plane perpendicular to the dividers of the grid attached to the surface of the grid that does not touch the plate when the grid is inserted into the apparatus, wherein the plane covers all of the through-holes of the grid. In various embodiments, the plane further comprises side planes perpendicular to said plane, said side planes parallel to and shorter in height than the dividers of the grid. In some embodiments, the grid further comprises offsetting features between the dividers and the plane.

In another aspect, the invention provides a method for performing multiple reactions (e.g., at the same time). The method includes (a) providing a system comprising (i) an apparatus comprising a plate comprising a number of elements having a first surface energy arranged in an array with an overlay having a second surface energy and a wall circumferential to the plate and (ii) a removable grid insertable into the apparatus to be positioned over the plate and within the wall of the apparatus, said grid comprising dividers enclosing a number of through-holes, said through-holes spaced in the grid to allow alignment of the through-holes of the grid over the elements in the plate when said grid is inserted into the apparatus, wherein said dividers of said inserted grid form wells bottomed by the plate and at least one element on said plate; (b) adding a first reagent-containing liquid through the through-holes of the grid of the system under conditions where the first reagent in the liquid adheres to the elements on the plate; (c) adding rinsing oil to said plate in an amount necessary to cover said plate; (d) draining excess rinsing oil from the plate resulting from step (c); (e) adding a liquid through the through-holes of the grid of the system, said liquid containing a second reagent suspected of reacting with the first reagent; (f) removing the grid from the apparatus; (g) washing the apparatus; and (h) detecting reaction of the second reagent with the first reagent. In some embodiments, the method further comprises inserting the grid into the apparatus following step (g). In some embodiments, step (h) is performed using a third reagent (e.g., a detectably labeled third reagent). In some embodiments, the third reagent is borne in a liquid.

In another aspect, the invention provides a method for performing multiple reactions (e.g., at the same time). The method includes (a) providing a system comprising (i) an apparatus comprising a plate comprising a number of elements having a first surface energy arranged in an array with an overlay having a second surface energy and a wall circumferential to the plate and (ii) a removable grid insertable into the apparatus to be positioned over the plate and within the wall of the apparatus, said grid comprising dividers enclosing a number of through-holes, said through-holes spaced in the grid to allow alignment of the through-holes of the grid over the elements in the plate when said grid is inserted into the apparatus, wherein said dividers of said inserted grid form wells bottomed by the plate and at least one element on said plate; (b) adding a first reagent-containing liquid through the through-holes of the grid of the system under conditions where the first reagent in the liquid adheres to the elements on the plate; (c) adding a liquid through the through-holes of the grid of the system, said liquid containing a second reagent suspected of reacting with the first reagent; (d) removing the grid from the apparatus; (e) washing the apparatus; and (f) detecting reaction of the second reagent with the first reagent. In some embodiments, the method further comprises inserting the grid into the apparatus following step (e). In some embodiments, step (f) is performed using a third reagent (e.g., a detectably labeled third reagent). In some embodiments, the third reagent is borne in a liquid.

In some embodiments, the first reagent is a cell (e.g., an adherent cell, a non-adherent cell, and a permeabilized cell. In some embodiments, the second reagent is an agonist (e.g., stimulator of the first reagent) or an antagonist (inhibitor of the first reagent).

In some embodiments, the first reagent is a binding agent. In some embodiments, the binding agent is a nucleic acid molecule (e.g., a single-stranded nucleic acid molecule), an antibody, and a ligand.

In yet another aspect, the invention provides an apparatus comprising: a plate comprising a number of elements, said elements each having an identical diameter and having a first surface energy, said elements arranged in an array in an overlay having a second surface energy, and a wall circumferential to the plate, wherein said overlay is a height over the elements of between about 5% and 100% of the diameter of the elements.

In some embodiments, the first surface energy results in a hydrophilic surface and the second surface energy results in a hydrophobic surface. In some embodiments, the height of the overlay over the elements is between about 10% and 80% of the diameter of the elements. In some embodiments, the height of the overlay over the elements is between about 20% and 50% of the diameter of the elements

BRIEF DESCRIPTION OF THE DRAWINGS

Those skilled in the art should more fully appreciate advantages of various embodiments of the invention from the following "Detailed Description of the Invention," discussed with reference to the drawings summarized immediately below.

DETAILED DESCRIPTION OF THE INVENTION

Figure 1A:
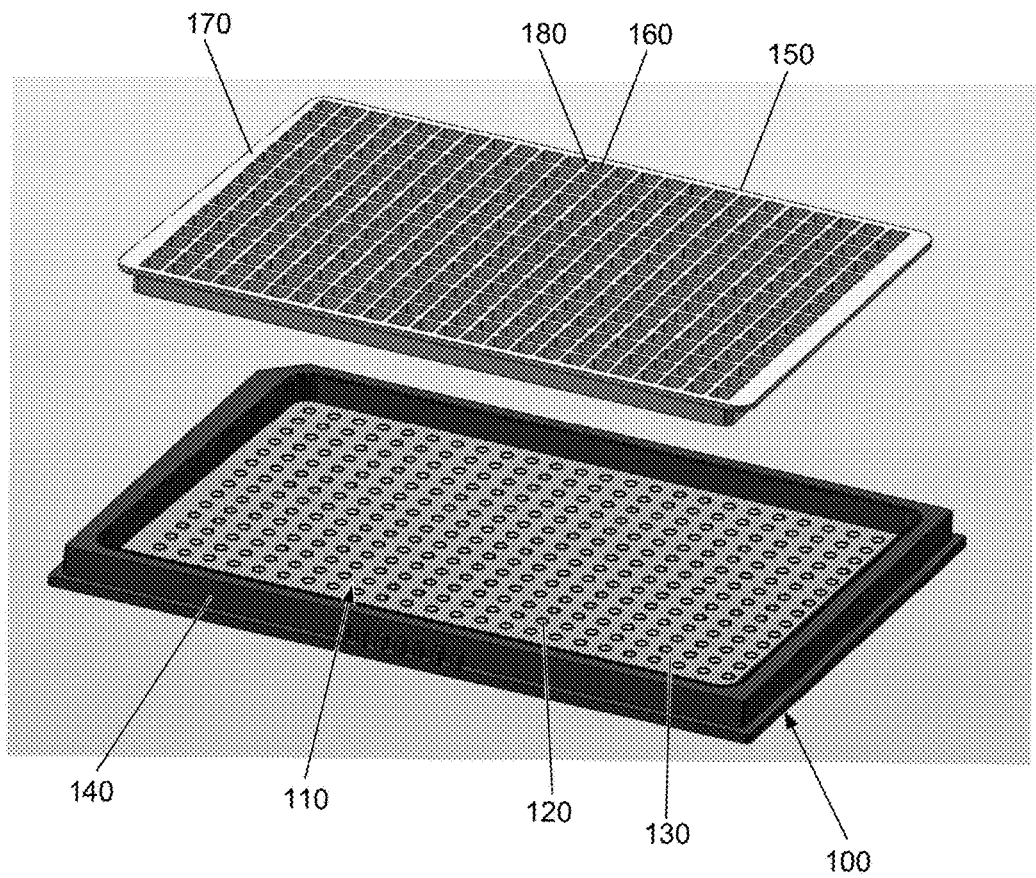
FIG. 1A is a schematic representation of an exploded view of a non-limiting system of the invention comprising an apparatus and a removable grid.

The invention provides apparatuses and methods for performing multiple reactions in small volumes of liquid. The invention provides the high-throughput capabilities of protein microarrays with the specificity and robustness of microtiter-plate assays such as ELISAs and cell proliferation assays.

The further aspects, advantages, and embodiments of the invention are described in more detail below. The patents, published applications, and scientific literature referred to herein establish the knowledge of those with skill in the art and are each hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology, biochemistry, chemistry, and immunology include Ausubel et al., *Current Protocols in Molecular Biology*, Wiley InterScience, New York, N.Y., (2007, and updates up to and including 2011); Coligan et al., *Current Protocols in Immunology*, Wiley InterScience, New York, N.Y., (2007, and updates up to and including 2011); Harlow and Lane, *Antibodies: A Laboratory Manual*, Cold Spring Harbor Laboratory Press, New York (1998); Lo et al., *Antibody Engineering: Methods and Protocols*, Humana Press, 2003; Sambrook et al., *Molecular Cloning: A Laboratory Manual,* 2nd Ed., Cold Spring Harbor Laboratory Press, New York (1989); and Kaufman et al., Eds., *Handbook of Molecular and Cellular Methods in Biology in Medicine*, CRC Press, Boca Raton (1995).

Microtiter plates allow running multiple reactions within multiple isolated compartments separated by physical walls. Many types of chemical, biochemical, and biological reactions and assays are performed on microtiter plates, particularly when multiple reactions are performed in high-throughput analyses. For example, during the generation of an antigen-specific monoclonal antibody (and antibody-secreting hybridoma cell) in accordance with the method Kohler and Milstein (see, e.g., *Nature* 256 (5517): 495-497, 1975), different individual clones of cells are grown in wells of microtiter plates. Antibody-containing supernatant taken from the wells are screening for their ability to bind to the antigen of interest, and the identified clone can then be expanded for large-scale production of the antigen-specific monoclonal antibody.

Similarly, small molecules are routinely screened in high-throughput cell-based reactions on microtiter plates to determine the candidate molecule to be further analyzed and formulated as a potential therapeutic. On a molecular level, screening of a potential therapeutic (e.g., a biological for its ability to antagonize an antigen-specific antibody or a ligand-specific receptor) are routinely screened using microtiter plates in assays such as ELISAs.

Many different types of microtiter plates are available commercially. However, while the presence of physical walls separating the different wells of the microtiter plate helps to prevent cross-contamination, the walls also hinder easy and convenient washing by flowing a bulk solution. Instead, an individual compartment needs to be washed one-by-one.

The apparatus described in PCT Patent Publication No. WO2008/06136 (also published as US patent publication no. 20100285573; incorporated herein by reference in its entirety) employs a virtual wall technology that enables running multiple reactions without physical walls. In this apparatus (a virtual wall plate and system is sold commercially under the trademark DropArray™ by Curiox Biosystem Pte. Ltd. (Signapore) or its distributors (e.g., Acelearium Lab Solutions, Inc., Westford, Mass., USA), instead of wells, hydrophilic elements are surrounded by a hydrophobic overlay. Liquids drops are thus held in place on the elements using surface energy effects. Such characteristics offer many advantages over standard microtiter plates including, for example, easy and convenient washing by flowing a washing solution across the surface of the apparatus.

It should be noted, however, a physical wall in a microliter plate does provide some benefits. For example, the presence of a physical wall between wells can expand the capacity of the volume that can be held in each well. In one model of the DropArray™ plate, an element (or well) of 2 mm diameter on the plate can hold a liquid up to 3 uL for typical handling. When the volume of a liquid increases beyond 3 uL, however, liquid can break off easily from the hydrophilic element. This is due to increased inertia (kinetic energy applied to a drop) coming from increased height of the drop while the cohesion of a liquid and adhesion between a liquid and hydrophilic surface remain same. By increasing the volume that each well (or element) can hold, each well could hold more sample, or have better detection of the sample or reaction product (e.g., where the detection reagent is borne in a liquid).

Another benefit provided by the presence of a physical compartment separated by a wall on a standard microtiter plate may be that the walls can facilitate dispensing of a liquid into individual wells. When dispensing onto a virtual wall plate (or another similar plate with shallow wells), where a well (also called an element) is defined by surface tension, the dispensed liquid should be delivered onto the feature relatively precisely onto the element. In contrast, when liquid is dispensed into a well separated by a physical wall, the dispenser can drop the liquid anywhere within a well.

The presence of physical walls may reduce the chance of spilling a fluidic content contained in a DropArray™ plate or a similar plate with extremely shallow wells. For example, in the configuration of DropArray™ technology, a plate contains an array of drops is immersed in inert fluid (e.g., the fluid sold under the trademark DropArray™ Rinsing Oil™ sold by Curiox Biosystem). When such plate with fluidic content is transported, the movement of the plate creates momentum in the fluidic content inside of a plate, which leads to an unblocked wave of fluid, often resulting in spillage when such wave reaches the end of the plate. The physical wall of the grid functions as a barrier dampening the unblocked flow of fluid.

Additionally, compartmentalization by a physical wall on a standard microtiter prevents accidental cross-contamination by displacement of a drop. When a drop is placed onto a hydrophilic element of a DropArray™ plate, the interaction between the drop and hydrophilic feature mostly result from hydrophilic-hydrophilic attraction, which is relatively weak. Therefore, a drop can be displaced relatively easily by external force, such as shear force generated by the flow of inert fluid present in the plate or physical shock applied from sudden movement of a plate.

Thus, for microtiter plates, there are benefits to having no physical walls (i.e., virtual walls), and benefits to having physical walls. Thus, it would be useful to have a virtual wall plate to which physical walls could be added or removed when desired. Thus, one aspect of the present invention thus stems from the development of a removable grid that can be inserted onto a virtual wall plate when the presence of physical walls is desired (e.g., during loading of sample or during incubation of the sample to allow a reaction to occur), and removed when the presence of physical walls is undesired (e.g., during washing of the plate). Surprisingly, the inventors discovered that when a grid made in accordance with the invention is inserted onto the virtual wall plate, a seal is formed thereby preventing cross-contamination between the wells created by the grid's physical walls. Indeed, if volumes within the well are small, if a drop on the hydrophilic element is displaced (e.g., if the plate is physically jarred), the drop is still contained within the area enclosed by the physical walls of the grid, thereby eliminating the possibility of cross-contamination into an adjacent well. Often such drop is attracted to a hydrophilic element again as the drop is surrounded by hydrophobic surfaces of the overlay, the inert fluid, and the physical wall of a grid. Additionally, the physical wall of a grid functions as a barrier and reduces the flow of an inert fluid within the plate, thereby minimizing the chance of a drop being displaced.

Accordingly, in a first aspect, invention provides a system comprising an apparatus and a removable grid insertable into apparatus. The apparatus may comprise a plate comprising a number of elements having a first surface energy arranged in an array within a thin overlay having a second surface energy; and a wall circumferential to the plate. In some embodiments, the first surface energy results in a hydrophilic surface and the second surface results in a hydrophobic surface. The removable grid insertable into the apparatus may be positioned over the plate and within the wall of the apparatus, where the grid comprises dividers enclosing a number of through-holes, the through-holes spaced in the grid to allow alignment of the through-holes of the grid over the elements in the plate when said grid is inserted into the apparatus, wherein said dividers of the grid inserted into the apparatus form sides of wells bottomed by the plate and at least one element on said plate.

In another aspect, the invention provides a removable grid insertable into an apparatus comprising a plate comprising a number of elements having a first surface energy arranged in an array within a thin overlay having a second surface energy and a wall circumferential to the plate, said grid comprising dividers enclosing a number of through-holes, said through-holes spaced in the grid to allow alignment of the through-holes of the grid over the elements in the plate when said grid is inserted into the apparatus, wherein said dividers of the grid inserted into the apparatus form sides of wells bottomed by the overlay of the plate and at least one element on said plate.

In a non-limiting example of the system and grid of the invention, a flat plate (e.g., a virtual wall plate) can be patterned with elements comprising molecules of interest to create an array. As described herein, the elements are surrounded by hydrophobic coating. The virtually flat plate with a hydrophobic overlay and hydrophilic element pattern within that overlay is similar to the surface characteristics of a typical array.

In some embodiments, the dividers of the grid have a second surface energy. In some embodiments, the second surface energy results in a hydrophobic surface.

In one non-limiting embodiment, a grid made of a hydrophobic plastic material such as polypropylene (PP) or polytetrafluoroethylene (PTFE) can be placed on the flat substrate to create 'removable' wells. In some embodiments in using one of the grids or the systems disclosed herein, the grid is placed on the substrate only during incubation. In some embodiments, the grid is placed on the plate during the loading step. During a washing step (or at other convenient times), the grid is removed from the plate in order to facilitate a whole plate washing without fluidic interruption from the presence of the grid.

Figure 1B:
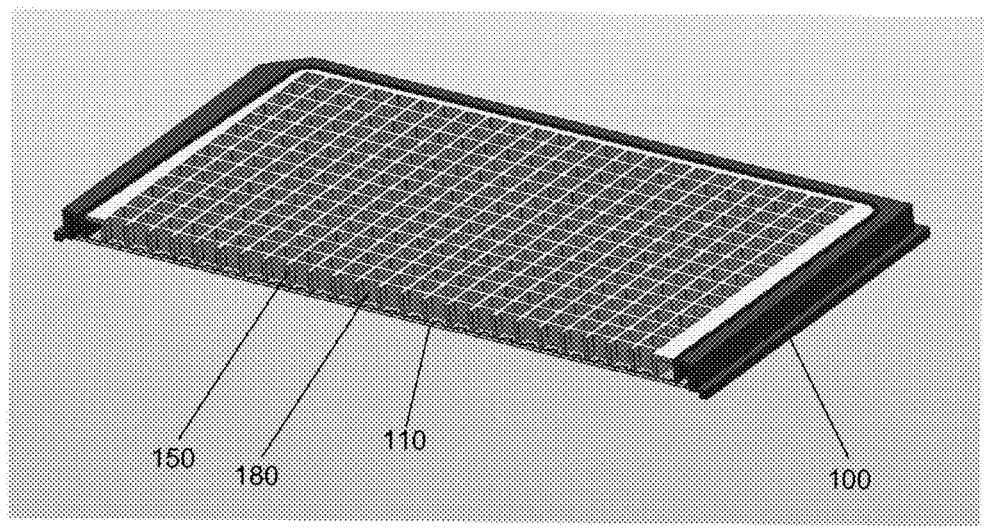
FIG. 1B is a schematic representation of an assembled sectional view of the system depicted in FIG. 1A.

One non-limiting example of a grid and system of the invention is shown in FIG. 1A, and FIG. 1B shows an assembled sectional view of the system of FIG. 1A. As shown in the exploded view of the system in FIG. 1A, an apparatus 100 has a plate 110 surrounded by a wall 140. The plate 110 has a plurality of elements 120 separated from each other by an overlay 130. The elements 120 and overlay 130 have a surface energy difference such that the elements 120 can each attract a liquid. For example, the elements 120 may be hydrophilic and the overlay hydrophobic so that aqueous liquids can be adhered to the elements 120 without cross contamination. The elements 120 may be transparent to aid in optical observation. The plate 100 may be used, for example, with the methods disclosed in PCT/SG2007/0003939, WO2008/063136, and WO2010/120249 (all of which are hereby incorporated by reference in their entirety). Note that the walls or exterior structure 140 of the apparatus shown in FIG. 1A allows for ease of manual or robotic handling and defines a reservoir above the plate 110. The reservoir can be used to hold a washing fluid (one that is miscible with liquid held on the elements 120).

A removable grid 150 (shown above the apparatus in FIG. 1A) can be inserted into the walls 140 of the apparatus to partition the reservoir created by the walls with dividers. The grid 150 shown in FIG. 1A includes a plurality of through-holes 160 that outlined by dividers 180, where the through-holes 160 have a spacing that corresponds to the elements of the plate 110. The grid 150 may fit snugly into the exterior structure (or wall) 140 so as to enforce positioning of the through-holes above the elements. The grid 150 may include handling structures 170. The handling structures 170 may be tabs that overhang the ends of the grid 150. In some embodiments, such handling structure 170 facilitates removal of the grid from the apparatus.

As shown by the interface between the plate 110 and the grid 150 in FIG. 1B, wells are created which are bottomed by the plate and walled by the dividers of the grid. As shown in FIG. 2, the plate forming the bottom of each well comprises at least one element within the well. One or more reagents may be added to the through-holes 160 to increase the volume of liquid that may be contacted with any given element 120 or to aid in the addition of different reagents to different elements.

Both the grid and exterior structure (i.e. walls) of the apparatus of the system of the invention may be made by injection-molding plastics by well known techniques. The plate of the apparatus may be, for example, made from glass patterned with a polytetrafluoroethylene (PTFE) material (e.g., the polytetrafluoroethylene (PTFE) sold under the trademark Teflon® by DuPont) such that the elements are hydrophilic (e.g., from the hydrophilic glass) while the overlay is hydrophobic (e.g., from the hydrophobic PTFE). FIG. 1 shows an example of the removable grid placed on top of a virtual wall plate. Note that the non-limiting plate shown in FIG. 1 has SBS (Society for Biomolecular Screening) standard 384 features (i.e., virtual wells or elements arranged in a 24×16 array). The non-limiting plate and apparatus of the invention depicted in FIG. 1A has 2 mm diameter hydrophilic elements. The external dimension of a grid fits the internal dimension of the walls of the apparatus such that when the grid can be inserted into apparatus (see FIG. 1B).

In the embodiment of the grid and system shown in FIGS. 1A and 1B, the pattern of the through-holes in the grid follows the pattern of the elements in the underlying plate exactly. In some embodiments, the dividers of the removable grid are, for example, 8.0-12.0 mm height. When the grid is inserted into the apparatus to create wells walled by dividers of the grid and bottomed by the plate comprising a single element, each well can hold liquid of up to 40-50 uL.

Note that although FIGS. 1A and 1B depict a DropArray™ virtual plate, other virtual wall plates similar to that shown in FIGS. 1A and 1B are commercially available, for example from Erie Scientific (a division of Thermo Scientific) and from Cytonix Corporation (Beltsville, Md., USA; sold under the trademark u-Plates™). The grid of the invention may be used inserted into apparatuses containing such virtual wall plates to create wells dividers of the grid and bottomed by the plate comprising at least one single element (i.e., single well with virtual walls).

It should be noted that one potential trouble in using a removable grid in the systems of the invention is cross-contamination between wells created walled by dividers of the grid and bottomed by the plate due to leaking of a fluid from one well to another well via a path under grid, as a grid is simply positioned on top of a bottom plate without sealing. The leakage of a liquid between wells can be controlled by adjusting the thickness of the walls and the surface tension of the grid. When the grid either is made of, for example polytetrafluoroethylene (PTFE) or polypropylene (PP), or is coated with such material on the surface, the surface of the grid presents significantly hydrophobic characteristics. The hydrophobic surface prevents the wetting of the grid by the liquid of a drop contained in each well. In some embodiments, the thickness of the grid dividers may be in the range of about, for example, 0.5-3.0 mm, or may be in the range of about, for example, 0.5-1.5 mm in thickness. The thickness of the grid dividers may be adjusted depending numerous factors including, without limitation, the physical characteristics of the liquid of a drop (e.g., how much reagent is borne by the liquid) and the diameter of the element. The thickness of the grid may also depend upon the presence of an inert fluid on the plate.

Thus, in some embodiments of the invention, the apparatus of the system further comprises an inert fluid that coats the plate with a thin layer. By "inert fluid" is meant a fluid that is immiscible with a hydrophilic liquid (e.g., water or a tissue culture media). Non-limiting examples of inert fluids of the invention include the perfluorinated hydrocarbon liquid sold under the trademark Fluorinert™ name by the 3M Corporation (St. Paul, Minn., USA) and the immiscible fluid sold by Curiox Biosystems (Signapore) under the trademark Rinsing Oil™. The presence of hydrophobic inert fluid can reduce the possibility of the leakage between neighboring wells in the presence of a hydrophilic liquid (e.g., a liquid bearing a reagent). The hydrophobic inert fluid thus makes a hydrophobic surface of a solid substrate such as PP and PTFE more resistant against wetting by a hydrophilic liquid.

In some embodiments, the inert fluid added to the plate of the apparatus after the plate has been loaded with a liquid containing a first reagent.

As used herein, by "reagent" is meant any molecule or vehicle (e.g., liposome, a living eurkaryotic or prokaryotic cell, or a non-living eukaryotic or prokaryotic cell) comprising at least one molecule. By "molecule" is meant any molecule including, without limitation, inorganic molecules and organic molecules (e.g., lipids, proteins, nucleic acid molecules, and carbohydrates).

In certain embodiments of the invention, the plate comprises a PTFE overlay patterned onto a hydrophilic surface such that flat hydrophilic elements are exposed (the virtual wells) that are surrounded by the PTFE overlay. In some embodiments, the diameter of each element is 2 mm, and each element is separated horizontally or vertically from its adjacent element by about 4.5 mm. In some embodiments, this results in a 384 array from a 16×24 element array (see FIG. 1A). In a non-limiting apparatus of the invention, the plate is contained within a wall that is approximately 8 mm in height. In some embodiments, the grid is constructed of polypropylene (PP). In some embodiments, the grid is made of polypropylene with 10-20% glass fillers in order to enhance mechanical strength of the material. Alternatively, the grid is made of metal, for example, such as aluminum, and coated with a hydrophobic resin, such as PTFE resin, in order to present a hydrophobic surface.

In some embodiments, the grid is made of metal or glass and coated with hydrophobic film (e.g., with PTFE or PP) in order to prevent it from floating on the inert fluid when inert fluid is added to the apparatus. Inert fluid has a high density. For example, the DropArray™ Rinsing Oil usually has a density of 1.5~2 g/ml, much higher than a typical plastic material such as polystyrene or polypropylene. Thus, it may be desirable to have the grid weigh more (e.g., be made of glass or metal) in order to prevent flotation.

In some embodiments, the grid is designed to sit inside of the reservoir of the plate tightly. In some embodiments, each divider of a grid has thickness of, for example, 0.5-2 mm with height of 5-10 mm. In some embodiments, each divider of the grid has a thickness of, for example, 0.5-1.5 mm with height of 7.5 mm. In one non-limiting embodiment of the invention, a grid may be optimized for the array format of a grid and the design of a corresponding plate. When the grid is made of a plastic material such as PTFE or PP, the grid can be produced by injection molding or a similar technique, which allows fabrication at reasonably low cost while maintaining precision required. When a grid is made of a metal such as aluminum, it can be produced by a general machining method available.

Figure 2A:
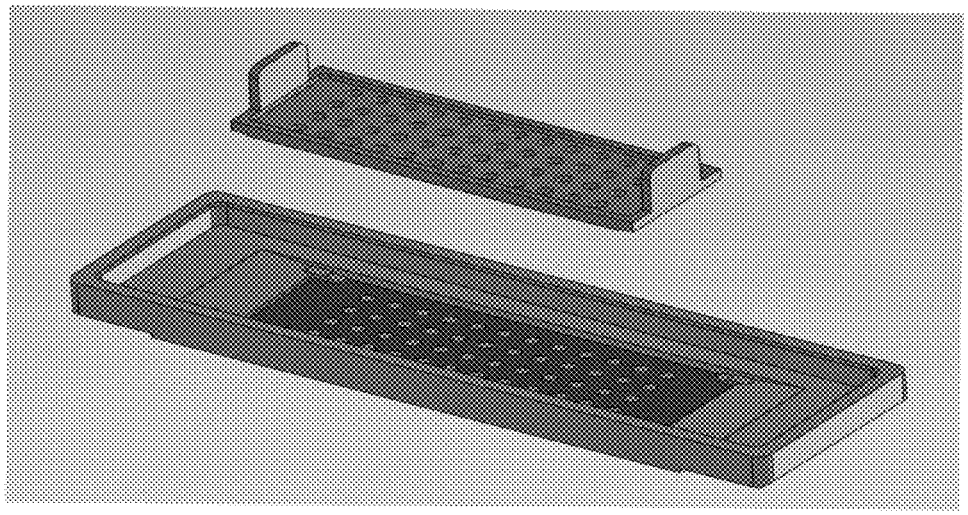
FIGS. 2A-2B are schematic representations showing exploded and assembled views of a non-limiting system of the invention, wherein the non-limiting removable grid depicted has large tabs for ease of handling.
Figure 2B:
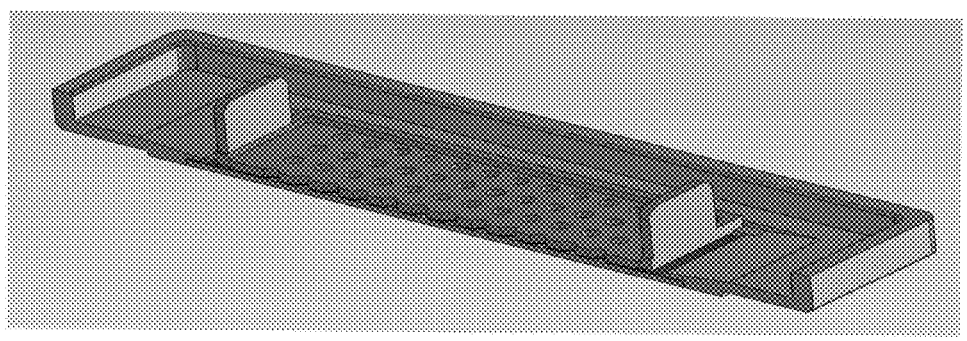

In another non-limiting embodiment of the grid and system disclosed herein, the grid further comprises handling structures that protrude upward from the grid when the grid is inserted into the apparatus (see FIGS. 2A and 2B). The handling structures (see FIGS. 1A-1B, and 2A-2B) provide a convenient grasp for user (e.g., a human or non-human user) grasp the grid and insert it or remove it from the apparatus of the system of the invention, as desired. Thus, in another embodiment of the invention, the grid further comprises at least one structure on the surface of the grid that does not touch the plate when the grid is inserted into the apparatus, said structure sized for a user to grab the grid and insert or remove the grid from the apparatus.

Thus, the insertion and/or removal of a non-limiting grid of the invention into or from an apparatus (e.g., a virtual wall plate such as Curiox Biosystem's DropArray™ plate) can be performed manually by a human user or automatically by an instrument. For example, an instrument can insert a grid into the apparatus by simply dropping the grid from above onto an apparatus such that the grid inserts into the walls of the apparatus and onto the plate of the apparatus. Then, the system containing the grid inserted into the apparatus can move around in a liquid handling system for addition of reagents. In one embodiment, once the dispensing of the reagent and incubation are completed, the system containing the grid inserted into the apparatus can be returned to the instrument, where the grid can be removed from the apparatus by, for example, picking up the grid (e.g., using the structure as described above) or flipping the entire plate upside down so that the grid will fall out of the apparatus under the influence of gravity. Once the grid is removed from the apparatus, the apparatus is ready for washing by a bulk washing solution instead of well-by-well wash.

Thus, as described above, in some embodiments of the invention, the plate comprises 48 elements of 2 mm diameter, where each element is separated by its horizontal and vertical neighbors by 4.5 mm. A removable grid fits snugly into the apparatus over the plate and within the walls. The apparatus may also have optional ramp structures allowing the grid to sit, for example, 0.1-0.2 mm higher than the surface of the plate in order to allow inert fluid to escape through the gap between the plate and grid upon dispensing of liquid into the through-hole of the grid. In this embodiment, the plate is coated with inert fluid by pouring inert fluid onto the plate and then draining the fluid off the apparatus. A coating of inert fluid will remain on the plate. The grid may also be pre-soaked with the inert fluid in order to prevent non-specific and/or irreversible adsorption of a reagent in the through-hole. In some non-limiting embodiments, the grid may be made of polytetrafluoroethylene (PTFE) and is total 4 mm high while the bottom 2 mm is the section with through-holes and the top 2 mm is the section with large reservoir to hold the inert fluid. At both ends of the grid shown in FIGS. 2A and 2B, there are two protrusions of 2-4 mm high in order to facilitate the handling of the grid in and out of the apparatus. In this non-limiting grid of the invention, 4-8 uL of a reagent is dispensed into each though-hole.

Figure 3A:
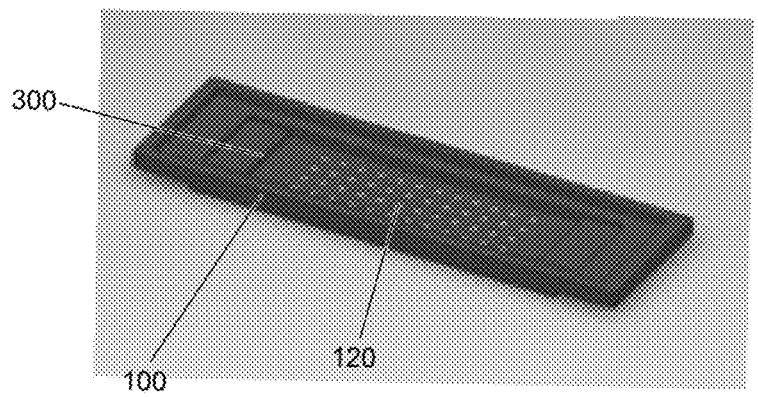
FIG. 3A is a schematic representation of a non-limiting apparatus of the invention having an elongate geometry.
Figure 3B:
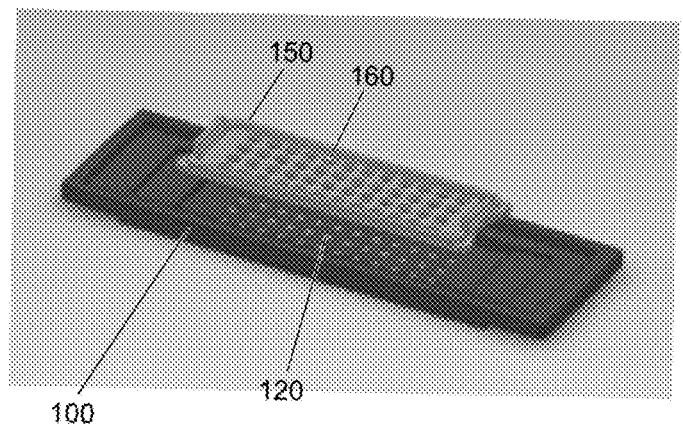
FIG. 3B is a schematic representation of an exploded view of the apparatus of FIG. 3A with a non-limiting removable grid of the invention.
Figure 3C:
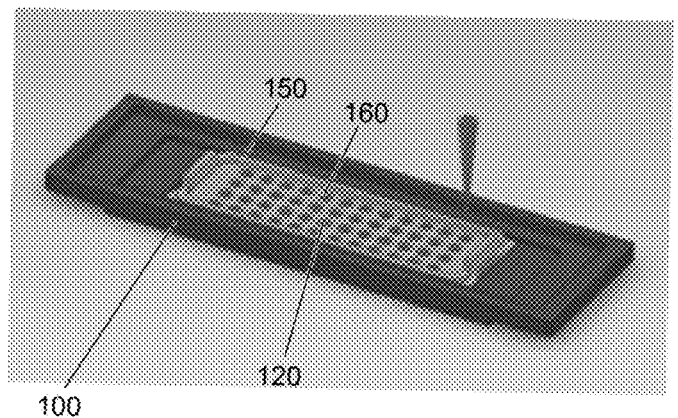
FIG. 3C is a schematic representation of an assembled view of the apparatus of FIG. 3A and the grid of FIG. 3B.

FIGS. 3A-3C shows another non-limiting system of the invention. In FIGS. 3A-3C, the apparatus 100 is elongate, in the general shape of a microscope slide. In the non-limiting apparatus 100 shown in FIGS. 3A-3C, the apparatus 100 further comprises one or more positioning structures 300 for positioning a grid 150 such that the through-holes 160 are aligned over the elements 120. FIG. 3C shows samples loaded into the system of the invention.

Accordingly, in another embodiment of the invention, the apparatus further comprises a positioning structure adjacent to the interior of the wall so as to guide alignment of the through-holes of the grid over the elements when the grid is inserted into the apparatus.

Figure 4A:
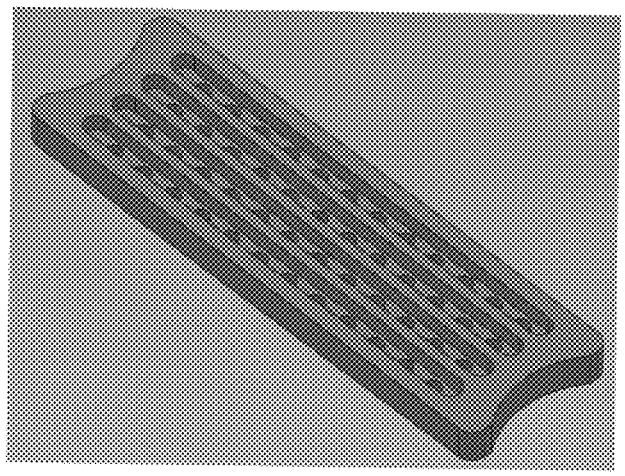
FIG. 4A shows a non-limiting embodiment of the removable grid of the invention where the removable grid has a reservoir connecting more than one through-hole of the grid.
Figure 4B:
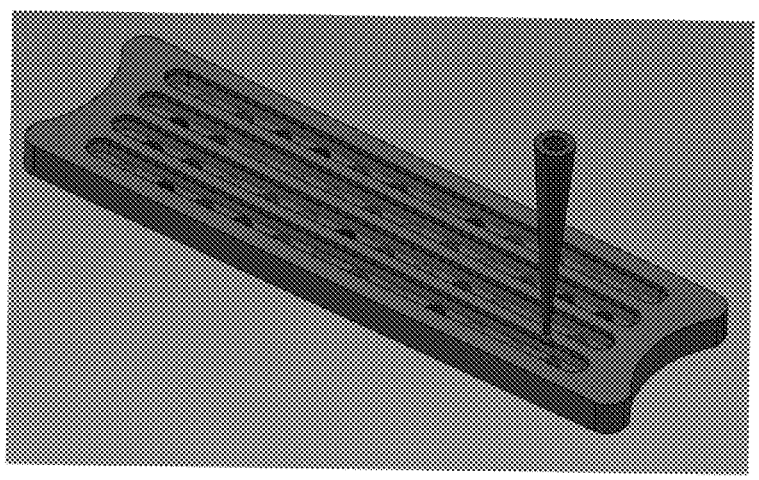
FIG. 4B shows the grid of FIG. 4A loaded with sample droplets.

To facilitate the loading of the apparatus of the invention with a reagent-carrying liquid, the through-holes of the grid may be joined in a larger reservoir, where the liquid may be added anywhere to the reservoir and allowed to flow into the through-holes to drop onto the elements of the underlying plate of the apparatus. FIGS. 4A and 4B show yet another non-limiting grid of the invention showing this reservoir. As shown in FIG. 4A, the dividers defining the through-holes are not rectangular but, rather, outline circular through-holes. A larger reservoir encompassing at least two through-holes facilitates addition of a reagent-bearing liquid to the underling plate when the grid is inserted into the apparatus (see FIG. 4B, where the droplet from the pipet-tip need not be exactly aligned with the through-hole in order to add the liquid to the element).

Accordingly, in another embodiment of the disclosed grid and system, the invention provides a grid further comprising a reservoir encompassing at least one through-hole of the grid, said reservoir on the surface of the grid that does not touch the plate when the grid is inserted into the apparatus.

A non-limiting embodiment of the grid disclosed herein can include features to minimize evaporation. For example, if the through-hole is small and holds less than 10 uL of a reagent, the reagent may experience evaporation during incubation. The evaporation of the reagent can be minimized by either building bigger through-holes to hold a bigger volume of a reagent, say more than 10 uL. Alternatively, the grid may have a built-in reservoir above the top surface that is structured to hold inert fluid. For example, in FIGS. 3A-3C, the grid comprises a reservoir that encompasses all the through-holes of the grid. In the embodiment shown in FIGS. 3A-3C, the reservoir is formed from an outer wall encompassing all the through holes and extending normal to the plane of the holes to a height sufficient to allow Rinsing Oil to cover liquid loaded in the holes. In FIGS. 4A-4B, numerous reservoirs, each encompassing more than one through-hole of the grid, are shown. In the embodiment shown in FIGS. 4A-4B, the grid can be designed with a series of long reservoirs at the top, where the inert fluid can be dispensed, effectively sealing off the reagent in the through-holes in the similar manner. Once the through-holes in the grid are filled with a reagent, inert fluid can be added into the reservoir, so that the reagents within the through-holes and/or on the elements of the plate are sealed by the inert fluid, thereby minimizing evaporation.

Of course, the skilled practitioner will realize that the through-holes need not be circular when combined with this reservoir feature. For example, one can easily imagine the square through-holes shown in the grid of FIG. 1 combined with the reservoir shown in FIGS. 4A-4B. Moreover, the reservoir may encompass all of the through-holes on the grid (see the grid of FIGS. 3B and 3C). Moreover to aid in directing the fluid to the droplet, one can easily appreciate that the dividers of the grid may also be funnel-shaped or sloped, such that a liquid droplet place into the reservoir (if present as in FIG. 4A-4B or in FIGS. 3B and 3C) or absent (as in FIG. 1) is directed to the element on the underlying plate.

Indeed, the shape of the well formed by the dividers of the grid as walls and bottomed by the plate may be readily changed for a better performance. For example, the physical shape of a grid divider may be in a rectangular shape. Alternatively, the shape may have a varying thickness, where the bottom of the divider very thin and the wall thickness increases in the upper part. The shape of a grid divider may be adjusted to fit the designed application best while considering the production cost. The shape of a grid divider with pointy bottom is expected to decrease the convection of the inert fluid present while the grid is being removed.

In some embodiments, the invention also provides for a grid and a system where each through-hole of the grid itself encompasses an array of elements on the plate when the grid is inserted into the apparatus of the invention. Microtiter plate analyses allow large numbers of probes or assays to query a given sample. However, users of an array (e.g., a microtiter plate or a virtual wall plate such as the DropArray™ plate) may have multiple or numerous samples to analyze against a fewer number of array elements than is present in a given array. This limitation is solved by yet another embodiment of the present invention.

Accordingly, in some embodiments, the invention also provides a removable grid with a lower number of through-holes than the number of elements on the plate of the apparatus into which the grid may be inserted. Thus, each through-hole of the grid is aligned over more than one element in the plate of the apparatus. Thus, portions of the arrayed elements of the plate can be exposed to different samples introduced through the through-holes of the grid.

Figure 5:
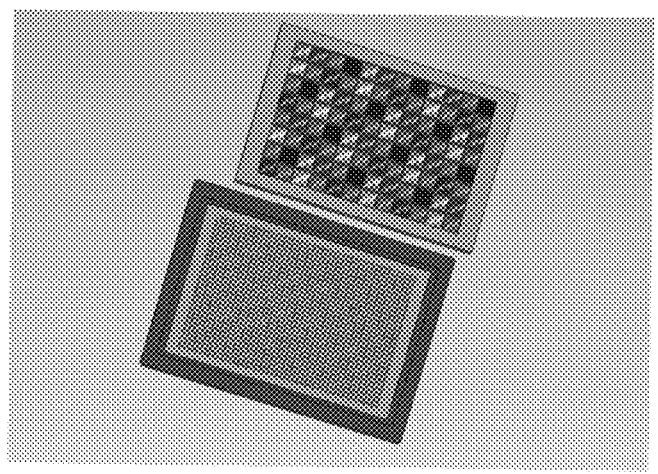
FIG. 5 is a schematic representation of a non-limiting system of the invention having an apparatus with a 1536-element plate configuration and a removable grid with 96 through-holes.
Figure 6A:
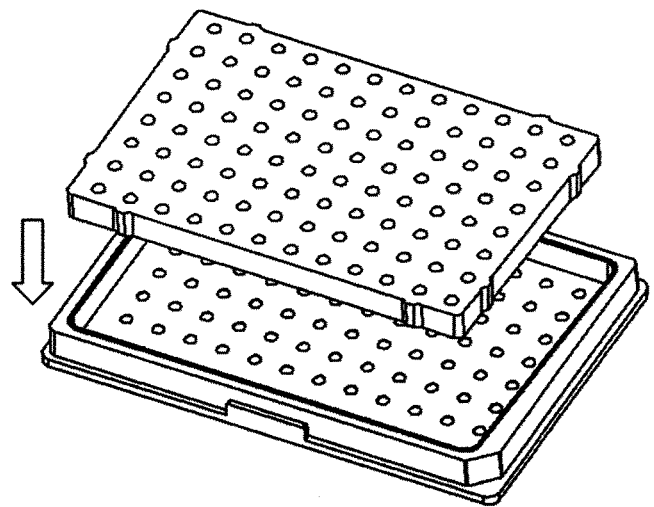
FIGS. 6A-6B are schematic representations showing exploded and assembled views of another non-limiting system of the invention have a 96-well microplate configuration.
Figure 6B:
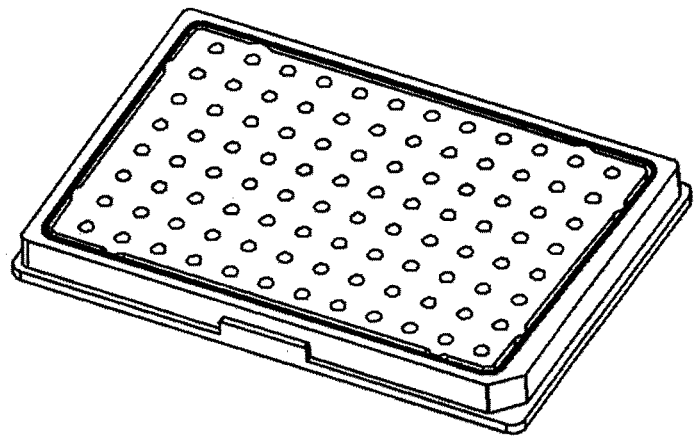
Figure 7A:
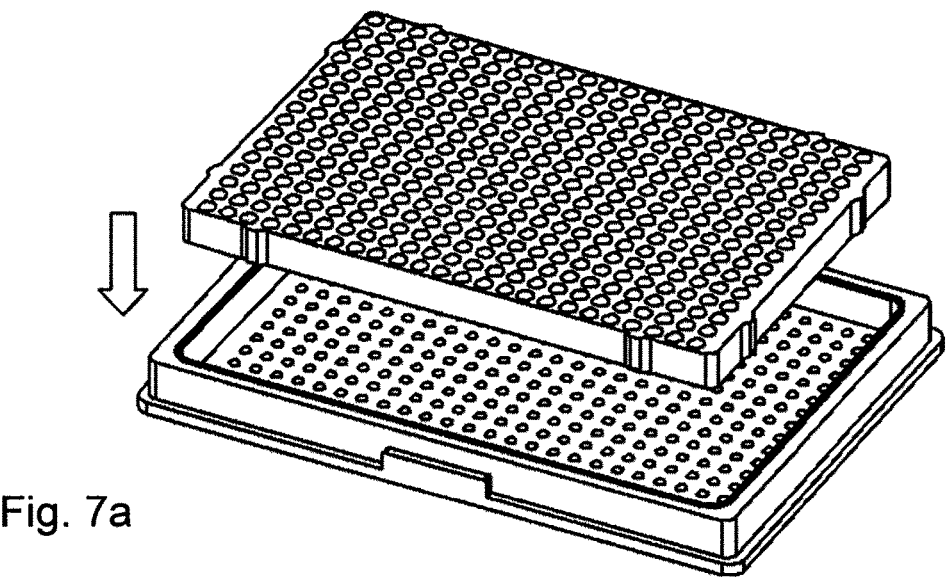
FIGS. 7A-7B are schematic representations showing exploded and assembled views of yet additional non-limiting system of the invention having a 384-well microplate configuration.
Figure 7B:
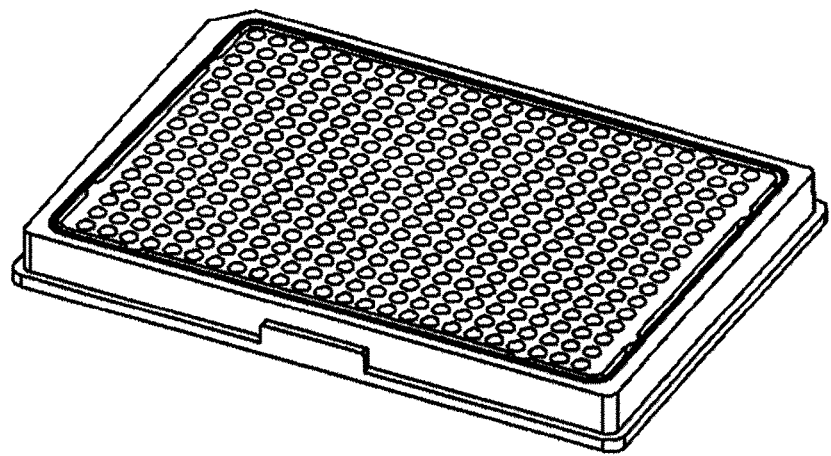

FIG. 5 shows a non-limiting example of this embodiment of a system of the invention. In FIG. 5, a removable grid with 96 through-holes is to be inserted into apparatus with a 1536-element plate configuration. Thus, each through-hole in the grid encloses 16 elements when the grid is inserted into the apparatus. The grid may contain a second reagent of a same kind or different kind as the reagent contained on the element of the plate, depending on the need. Thus, each of those 16 elements can be exposed to the same second reagent at the same time in a multiple reaction. In such configuration, the user can obtain up to 1536 data points with tools compatible with 96-well format, which can be easily found in a typical research laboratory.

This array within an array configuration of a grid and/or system of a non-limiting embodiment of the invention is useful for high through-put screening. For example, it may be desirable to screen sixteen different types of antibodies for their varying abilities to bind an antigen. The sixteen antibodies can be patterned 96 times onto the 1536-element plate of the apparatus. Upon insertion of the grid into the apparatus, 96 different potential antigens can be added through the through-holes onto the apparatus. Because of the hydrophobic spaces between the elements (with or without coating of the hydrophobic overlay with an inert fluid), the potential antigen-containing liquid will pool onto the elements containing the antibodies. After removal of the grid, washing of the plate, and replacement of the grid, detection of binding of the antibody to the potential antigen can be determined using conventional detection methods. For example, binding can be detected incubating the system with a detectably labeled anti-antigen antibody and detecting binding of the anti-antigen antibody.

As used herein, by "detectably labeled" is meant that a reagent is labeled with a detectable entity. For example, the reagent may be radioactively labeled (e.g., with $^3H$, $^{32}P$, $^{14}C$, or $^{35}S$), fluorescently labeled (e.g., with fluorescein or phycoerythrin), or labeled with a entity that is detectable upon addition of a detectable substrate (e.g., labeled with horse-radish peroxidase).

Of course in using any of the grids or systems of the invention, the number of reagents can be adjusted and designed conveniently depending on analysis needs. For example, the number of reagents can be determined by the design of an array—the size of each element (or spot) for each reagent and the pitch (i.e., distance between element (or spots). In the example of using standard microtiter plate size as a plate (available from Society of Biomolecular Sciences), the array can follow the standard specification of a 1536 well microtiter plate (See FIG. 5). Each element of, for example, 1 mm diameter, is separated by its horizontal and vertical adjacent elements by 2.25 mm.

As described above, a non-limiting embodiment of a removable grid of the invention may facilitate the dispensing of a liquid-borne reagent onto each element of the plate of the apparatus. In some embodiments, an inert fluid (e.g., Rinsing Oil available from Curiox Biosystems) is added into the plate and drained in order to wet the surface of the plate. Then, a removable grid is positioned inside the apparatus as shown in FIG. 1B. A reagent solution is added into each well walled by the dividers of the inserted grid and bottomed by the plate by, for example, pipetting. With the presence of a physical well created by the grid, it may be easier to dispense a reagent. Further because of the physical wall, even if the droplet is not placed precisely onto the element, the wall will prevent the droplet from cross-contaminating the droplet on an adjacent element. Due to the hydrophobicity of the overlay and the grid dividers, the droplet will be attracted to the hydrophilic element and will remain there.

In addition to aiding in dispensing a liquid-borne reagent onto the elements of the plate of the apparatus, the disclosed grid of the invention detection of a reaction result at the end of an assay process. For example, when an ELISA assay is run on a virtual wall plate (e.g., the apparatus described herein or a DropArray™ plate), the last step of the ELISA process is detection of binding of the sample to the plate. Of many detection methods currently available, absorbance (e.g., using a colorimetric detectable label) and luminescence (e.g., using a fluorescent detectable label) are popular. In these particular methods, the quality of detection such as sensitivity and signal-to-background ratio may be affected by the volume of the liquid-borne detectably labeled reagent. FIGS. 6A-7B and 7A-7B show examples of a 96 well system and a 384 well system, respectively, where a removable grid inserted into an apparatus can produce physical wells for adding increased volume of a detectably labeled reagent on top of a hydrophilic element. In other words, the removable grid can help to increase the volume of a detectably labeled reagent per well beyond what is practical without the grid.

In such case of volume-dependent detection, the ratio of the surface area of a hydrophilic element and the volume of a detecting reagent may affect the quality of the data. In other words, the simple increase of the volume of a detecting reagent may not generate enough signal increase due to the limited surface area of a hydrophilic element, e.g., due to the number of active protein available on the surface of a hydrophilic element. When such challenge occurs, the shape of a grid through-hole can be the shape of upside-down funnel. For example, the bottom of the grid through-hole may have the same diameter as that of a hydrophilic element. Then, there is a slope to reduce the diameter of the through-hole quickly, for example at 25-85 degree. After the slope, the diameter of the through-hole stays smaller than that of the hydrophilic element. At the detection of absorbance, the smaller diameter of the through-hole may be either same as that of the detecting light beam or up to 50% bigger.

In an alternate embodiment of the invention, the through-holes of the grid may have a diameter that is the same as or not significantly larger or smaller than the diameter of the element of the apparatus. In this embodiment, the grid can be pre-loaded with the reagent-bearing liquid prior to its insertion into the apparatus. In this embodiment, the liquid loaded into the grid should be able to stay within the through-hole (and not simply flow out due to gravity) if the size of the through-hole and surface tension of the inner surface are optimized to overcome the downward force of gravity. When the grid is inserted into the apparatus, the liquid in the grid will be attracted to the hydrophilic element and will adhere to the element of the plate and not the through-hole of the grid.

In some embodiments of the invention, the grid further comprises offsetting features on the surface of the grid that touches the plate when the grid is inserted into the apparatus. These offsetting features allow the grid to sit upon the second surface energy overlay on the surface of the plate of the apparatus, but without sealing firmly to the plate due to surface tension. The discovery of the applicability of such offsetting features was realized when the user had difficulty removing the grid from the apparatus without dislodging or jarring the apparatus such that the liquid droplets on the elements were dislodged. The seal between the grid and the second surface energy overlay on the surface of the plate of the apparatus can be altered depending upon whether the plate or the grid or both had been previously rinsed (and hence coated) with inert fluid. The offsetting features also allow the easy removal of excess inert fluid to be drained off the apparatus without having to remove the inserted grid.

Accordingly, in some embodiments, offsetting features are present on the surface of the grid that touches the plate of the apparatus when the grid is inserted into the apparatus. Interestingly, when such a grid with offsetting features is inserted into the apparatus, the well created which is walled by the dividers of the grid and bottomed by the plate may be as capable of holding liquid within the well as a grid without offsetting features. This is likely due to the shallowness of the offsetting features and/or the hydrophobic energies of the grid and the overlay of the plate and, optionally, in the presence of inert fluid.

In further embodiments of the invention, the grid further comprises a plane perpendicular to the dividers of the grid attached to the surface of the grid that does not touch the plate when the grid is inserted into the apparatus, wherein the plane covers all of the through-holes of the grid. The plane (or lid) covers the entire apparatus when the grid is inserted into the apparatus. In some embodiments, the plane further comprises side planes perpendicular to said plane, said side planes parallel to and shorter than the dividers of the grid. In some embodiments, the grid further comprises offsetting features between the dividers and the plane.

A plate is often covered with a lid to protect a fluidic content inside. For example, a microtiter plate, which is popular in running multiple reactions in a given footprint, comes with a lid to prevent evaporation and protect the content inside from contamination by the surrounding. At present, in most microtiter plates, fluidic content is contained in an array of small compartments divided by physical walls, for example, in a manner of 24, 96, 384, and 1536 well format. The primary function of the physical walls is to separate the fluidic content from each other in order to prevent cross-contamination.

When a plate (such as the apparatus described herein) is designed without a physically dividing wall in a hollow pocket, e.g., a hollow reservoir with a flat slide at the bottom, a conventional lid leads to easy spilling of a fluidic content. This is because there is no barrier (such as a physical wall) to dampen the generation of a wave produced by fluidic content within a plate. When the wave is formed during transportation, a relatively tall wave of the fluid collides with the side wall and lid and leads to the leakage of the content. Furthermore, waves of inert fluid inside may displace a drop from a hydrophilic feature. The displaced drop can easily move around and merge with a drop on another hydrophilic feature, leading to cross-contamination.

In one embodiment of the present invention, a lid comes with a grid of physical walls attached to the flat, wide part of a lid in a perpendicular manner. In this non-limiting embodiment of the invention, the grid-attached a lid provides benefits similar to those of a removable grid described earlier. The grid of physical walls functions as a barrier against the flow of the fluidic content, particularly in a hollow plate, reducing the spilling of fluidic content by, for example, accidental shaking. In addition, an accidentally displaced drop will be confined within a compartment created by the grid without the possibility of merging with a neighboring drop. In fabrication of a lid, a wide, flat, often transparent area is preferably made of transparent polystyrene, polycarbonate or similar material for optical clarity. A grid attached to the flat area is preferably made of hydrophobic polypropylene (PP), polytetrafluoroethylene (PTFE) or similarly hydrophobic material. Although the grid is described here as attached, the grid-attached lid can be a monolithic structure, or multiple structures adhered or welded together, depending on the manufacturing strategy, several or which are well-known in the art.

In some embodiments of the invention, the lid attached to the removable grid is simply a typical lid that is attached to all (or most) of the surfaces the dividers of the grid that do not contact the apparatus when the grid is inserted into the apparatus. In some embodiments, the lid (with attached grid) simply sits on the apparatus by gravity, where the inner surface of the lid touches all (or most) of the top of the walls of the apparatus.

It should be noted that depending on specific intended application, in some embodiments, a lid of the invention may come with additional features. For example, a lid may come with a gasket and little protrusions to grab in order to provide water-tight or nearly water-tight sealing against a plate when assembled. In an example of automation, it should be easy and simple to place or remove a lid in and out of a plate in a simple automation process, for example, by a robotic arm. In an application for cell-based assays, often the plate assembled with a lid is required to allow sufficient air exchange between the external and internal ambience and between different compartments within a plate. In such application, it is important that a lid is built with designs and features that ensure necessary air exchange occurring.

Figure 8A:
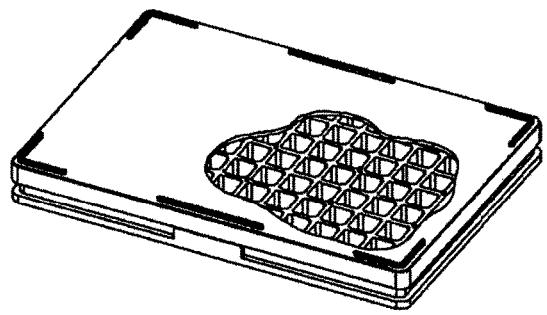
FIG. 8A is a schematic representation showing a cutaway view of a non-limiting embodiment of the invention having an apparatus and a non-limiting grid comprising a lid with baffles.
Figure 8B:
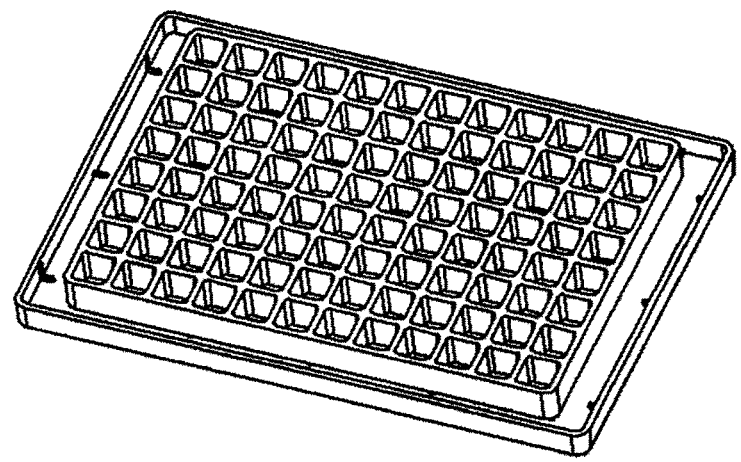
FIG. 8B is a schematic representation showing an underside view of the lid of FIG. 9A.
Figure 8C:
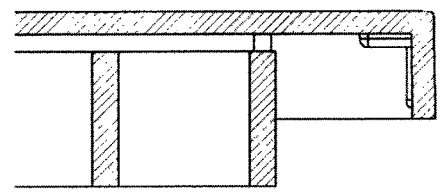
FIG. 8C is a schematic representation showing a close-up sectional view of a portion of the lid of FIGS. 8A-8B, showing baffles (i.e., offsetting features) which create an air gap between the lid and the grid.

The physical walls (i.e., dividers of the grid) that are attached to the flat, wide area of a lid may come with a range of format, 24, 96, 384, and 1536. The thickness of the dividers can range, for example, from 0.5 mm to 3 mm, depending on the format and the size of hydrophilic elements of the plate. FIGS. 8A-8C show a non-limiting example of a lid for the format of a 96-well microarray. FIG. 8A shows a cutaway view of the lid. In this non-limiting embodiment, the dividers of the grid are attached to the lid through small contact points such as projected columns. FIG. 8B shows the lid of FIG. 8A upside down, and FIG. 8C shows a cross-sectional view of the lid of FIG. 8A showing offsetting features (e.g., baffles) that create an air gap between the flat part and grid part.

In one embodiment of fabrication, a grid may be made of PP, preferably with 10-20% glass fillers for PP, in order to enhance mechanical strength of the material, or PTFE for its superior hydrophobicity. Alternatively, a grid is made of a metal, for example, such as aluminum, and coated with a hydrophobic resin, such as PTFE resin, in order to present a hydrophobic surface. In some embodiments, a grid may be designed to sit inside of the reservoir of the plate tightly. The wall of a grid has thickness of, for example, 0.5-3 mm, with a height of 5-10 mm, optimized for the array format of a grid and the design of a corresponding apparatus. In some embodiments, when a grid is made of a plastic material such as PTFE or PP, the grid can be produced by injection molding or a similar technique, which allows fabrication at reasonably low cost while maintaining required precision. In some embodiments, when a grid is made of aluminum, it can be produced by general machining method available. The fabricated grid is then attached to a flat lid part by various adhesion methods such as gluing, ultrasonic bonding, etc. In some embodiments, a lid part may be made of a transparent or non-transparent material such as glass, metal, and a wide range of plastic materials. In some embodiments, a lid part may be made of a transparent plastic material such as polystyrene, polycarbonate, or cyclic olefin copolymer. The lid part can also be produced by injection molding or a similar technique, which allows fabrication at reasonably low cost while maintaining precision required.

In another embodiment, the contact point between the barrier and the flat, wide area of a lid may be not completely sealed. For example, the contact of the flat part and grid can be made through small columnar spacers when airflow in and out of the assembled plate is necessary for an intended application; for example, working with aerobic cell cultures. These air gaps facilitate the airflow between different compartments and external ambience in a similar manner to what would happen in a conventional microtiter plate during a similar application. As a result, cell-based assays may be performed without stressing or killing the cells or skewing the results due to differential aeration of different features.

Alternatively, when the lid is used for an application such as ELISA, where the airflow is not required, such air gap between the flat part and grid of a lid is unnecessary. Accordingly, in some embodiments, the grid part may directly contact the flat part without any air gap between them.

In addition, in some embodiments when the grid with attached lid is assembled with the apparatus, the grid divider may extend far enough (i.e., have enough height) to contact the plate or be in close proximity to the plate, for example less than 2 mm apart. However, if the distance between the end of the grid divider and the plate is too big, two potential problems may arise: 1) flow of inert fluid under the grid divider on the surface of the plate is not reduced enough to minimize the associated problems such as spill of fluid and displacement of drops by the resulting shear force and 2) accidentally displaced drops may move from its original compartment to a neighboring compartment in the gap between the grid divider and the surface of the plate leading to cross-contamination.

Figure 9:
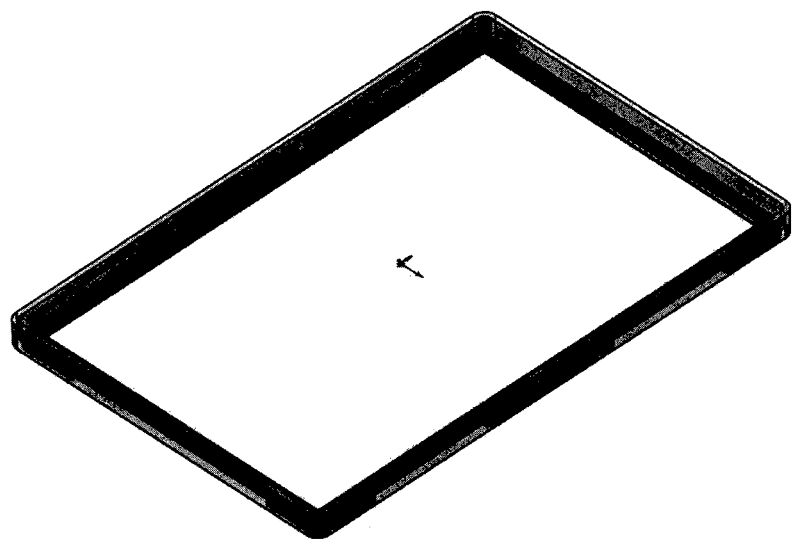
FIG. 9 is a schematic representation showing an alternate non-limiting lid for airtight sealing.

Thus, in some embodiments, air exchange is not desirable at all, and it may be desirable to keep a plate covered with a lid air-tight and leak-free or a lid simply without any physical spacers. Thus in another embodiment, the invention provides an apparatus covered with a grid-attached lid, where the lids is air-tight and leak-free on the apparatus. FIG. 9 shows an embodiment of an air-tight, leak-free grid and lid of the invention. As shown in FIG. 9, the air-tight lid comes with two catches on both long sides to snap fit to apparatus and rubber seal on bottom side of lid to create tight fit. Basically, the tight fit feature will block the fluid spillage and minimize the evaporation of fluid in the plate. At the same time, the lid can be still designed to be stackable. To aid in showing the rubber seal and the catches to snap onto the apparatus, the grid attached to the lid is not shown in FIG. 9.

In yet another embodiment, a grid of the invention with a lid attached may be configured to accept an inert fluid into the apparatus while the lid remains assembled with the apparatus. FIGS. 10A-10D show a lid modified from the version described above and depicted in FIGS. 8A-8C. As with the previously described grid with a lid, FIG. 8A shows the lid with a flat part with an attached grid. As with the previously described grid with attached lid, the grid can have optional small, protruding columns that ensure a gap between the lid and the grid for facilitating airflow (see FIG. 10B). The lid-grid structure can also have offsetting features (e.g., tabs or baffles) that offset the lid from the plate to create an air-flow gap (see FIG. 10D). Alternatively, the tabs can be on the wall of the apparatus.

Figure 10A:
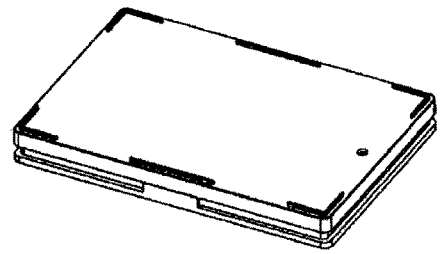
FIG. 10A is a schematic representation showing a cutaway view of a non-limiting embodiment of the invention having an apparatus and a non-limiting grid comprising a lid with baffles and a hole for introducing fluid (e.g., inert fluid)
Figure 10B:
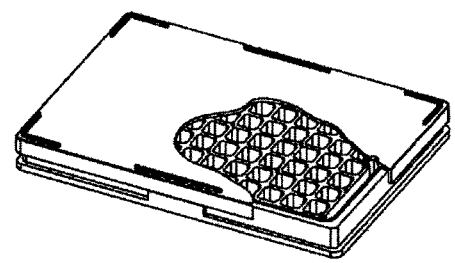
FIG. 10B is a schematic representation showing a cutaway view of the lid of FIG. 10A showing the reservoir surrounding the hole.
Figure 10C:
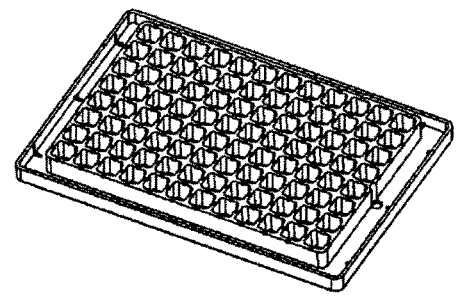
FIG. 10C is a schematic representation an underside view of a lid of FIG. 10A.
Figure 10D:
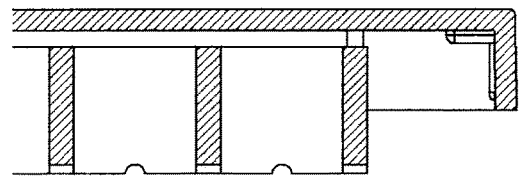
FIG. 10D is a schematic representation a close-up sectional view of a portion of the non-limiting lid of the invention depicted in FIGS. 10A-10C, the grid having notches on the surface of the grid that touches the plate of the apparatus in the assembled system.

The grid with attached lid shown in FIGS. 10A-10D has three notable modifications from the grid with attached lid shown in FIGS. 8A-8C. First, at one side of the lid, there is a small through-hole of 1-3 mm, where inert fluid may be added by, for example, a pipette. The through-hole can be seen in the FIG. 10A, toward the right side. Second, right below the through-hole, there is a long, narrow chamber between the sidewall of the plate and the first divider of the grid (as shown in FIG. 10B). Upon the addition of inert fluid (e.g. a perfluorocarbon DropArray™ Rinsing Oil as mentioned above), the fluid is first transferred to this chamber before spreading out through the entire plate. This chamber functions to lower resistance to added the fluid. Third, at the bottom of the grid walls, there are small notch-like openings of, for example, semicircular shape of 0.5 mm-3 mm diameter. The notches allow for fluid communication between "wells" of the plate when the grid with attached lid is inserted into the apparatus. When the fluid is added through the small through-hole, it may spread throughout the entire plate by passing through the semicircular opening and/or gap between the end of the grid and the flat slide of a plate if there is any gap between the grid and the flat slide. However, the notches can be small enough so as to retain the anti-wave features of the lid. It is notable that a semicircular notche is present at the end of the divider of a grid in both x- and y-direction.

The addition of the fluid while the lid is assembled with the plate provides a few advantages. First, the potential displacement of adhered drops by the flow of the fluid is minimized, as the flow of the liquid through the small gaps is designed to be gentle. Second, a displaced drop, which could happen by any physical shock or sudden movement, will be confined within the original compartment, preventing cross-contamination.

In a further aspect, the invention provides a method for performing multiple reactions in parallel, the method comprising (a) providing a system comprising (i) an apparatus comprising a plate comprising a number of elements having a first surface energy arranged in an array with an overlay having a second surface energy and a wall circumferential to the plate and (ii) a removable grid insertable into the apparatus to be positioned over the plate and within the wall of the apparatus, said grid comprising dividers enclosing a number of through-holes, said through-holes spaced in the grid to allow alignment of the through-holes of the grid over the elements in the plate when said grid is inserted into the apparatus, wherein said dividers of said inserted grid form wells bottomed by the plate and at least one element on said plate; (b) adding a first reagent-containing liquid through the through-holes of the grid of the system under conditions where the first reagent in the liquid adheres to the elements on the plate;

(c) adding rinsing oil to said plate in an amount necessary to cover said plate; (d) draining excess rinsing oil from the plate resulting from step (c); (e) adding a liquid through the through-holes of the grid of the system, said liquid containing a second reagent suspected of reacting with the first reagent; (f) removing the grid from the apparatus; (g) washing the apparatus; and (h) detecting reaction of the second reagent with the first reagent. In some embodiments, the method includes inserting the grid into the apparatus between steps (g) and (h). In some embodiments, step (h) is performed using a third reagent. In some embodiments, the third reagent is detectably labeled.

In a further aspect, the invention provides a method for performing multiple reactions in parallel, the method comprising (a) providing a system comprising (i) an apparatus comprising a plate comprising a number of elements having a first surface energy arranged in an array with an overlay having a second surface energy and a wall circumferential to the plate and (ii) a removable grid insertable into the apparatus to be positioned over the plate and within the wall of the apparatus, said grid comprising dividers enclosing a number of through-holes, said through-holes spaced in the grid to allow alignment of the through-holes of the grid over the elements in the plate when said grid is inserted into the apparatus, wherein said dividers of said inserted grid form wells bottomed by the plate and at least one element on said plate; (b) adding a first reagent-containing liquid through the through-holes of the grid of the system under conditions where the first reagent in the liquid adheres to the elements on the plate;

(c) adding a liquid through the through-holes of the grid of the system, said liquid containing a second reagent suspected of reacting with the first reagent; (d) removing the grid from the apparatus; (e) washing the apparatus; and (f) detecting reaction of the second reagent with the first reagent. In some embodiments, the method includes inserting the grid into the apparatus between steps (e) and (f). In some embodiments, step (f) is performed using a third reagent. In some embodiments, the third reagent is detectably labeled.

In some embodiments, the first reagent is a cell (e.g., an adherent cell, a non-adherent cell, and a permeabilized cell). In some embodiments, the second reagent is an agonist or antagonist.

In some embodiments, the first reagent is a binding agent. By "binding agent" is meant a molecule that can bind with specificity to another molecule (including, for example, a molecule on a cell). Thus binding agents include, without limitation, nucleic acid molecules (which can bind by hybridizing to nucleic acids with complementary sequences), antibodies (which can specifically bind to their antigen), receptors (which can specifically bind to their ligand or partner receptor), ligands (which can specifically bind to their receptors), specific tags (e.g., his-tags which specifically bind to nickel ion-containing molecules), and individual member of a binding pair (e.g., streptavidin and biotin will specifically bind one another).

In using the various apparatuses and grids described herein, the inventors surprisingly discovered that non-adherent (i.e., suspension cells) were retained on the apparatus without the grid when the height of the overlay over the elements on the plate was at least 5% of the diameter of the elements. As described below in Example II and IV, this discovery facilitates the use of the various embodiments of the invention with reactions using suspension cells.

Accordingly, in still a further aspect, the invention provides an apparatus comprising a plate comprising a number of elements, said elements each having an identical diameter and said elements having a first surface energy, where the elements arranged in an array in an overlay having a second surface energy, and a wall circumferential to the plate, wherein said overlay is a height over the elements of between about 5% and 100% of the diameter of the elements.

This aspect of the invention stems from the discovery that when suspension cells are "plated" into the apparatus (with or without the aid of a grid inserted into as described herein), the suspension cells can be retained in the apparatus if the overlay has a height above the elements of at least 5% of the diameter of the elements. For example, in a standard 384 element array, each element has a diameter of 2 mm. Thus, the height of the overlay in this aspect of the invention is at least 0.1 mm over the elements.

Of course this height can vary. For example, in some embodiments, the height of the overlay over the elements is between about 10%-80% of the diameter of the elements (e.g., for a 2 mm diameter element, the height of the overlay is between about 0.2 mm and 1.6 mm). In some embodiments, the height of the overlay over the elements is between about 20% and 50% of the diameter of the elements (e.g., for a 2 mm diameter element, the height of the overlay is between about 0.4 mm and 1 mm).

As described below, having an apparatus with an overlay height over the elements of at least 5% of the diameter of the elements is useful for retaining suspension cells on the apparatus during washing (e.g., where the elements are tissue culture treated).

In various embodiments of all aspect of the invention, the elements of the apparatus may be tissue culture treated. Thus, the flat apparatus and/or the apparatus comprising an overlay with a high over the surface of the elements of at least 5% of the diameter of such elements described herein may have tissue culture treated elements.

Methods to tissue culture treat surfaces are well known and include, without limitation, exposure of the surface to a vacuum-gas plasma tissue culture treatment process and exposure of the surface to corona discharge. These processes generate highly energetic oxygen ions which graft onto the surface (e.g., where the elements of the plate are made of polystyrene, the highly energetic oxygen ions graft onto polystyrene chains) so that the surface becomes hydrophilic and negatively charged when tissue culture media or water is added (see, e.g., Hudis, M. Plasma Treatment of Solid Materials. In: *Hollahan, J. R.; Bell, A. T.; Ed. Techniques and Applications of Plasma Chemistry*. John Wiley and Sons, New York; 113-147, 1974; Adaption of Plastic Surfaces for Tissue Culture by Glow Discharge. J. Clinical Microbiology 2: 46-54; 1975. Andrade, J. D., Ed. Surface and interfacial Aspects of Biomedical Polymers. Vol. 2, New York, Plenum Press 1985; and Ramsey et al., Surface Treatments and Cell Attachment, In Vitro, Vol. 20: 802-808; 1984). The more oxygen that is incorporated on to the surface the more hydrophilic it becomes and the better it is for cell attachment and spreading.

The following examples are provided to illustrate, but not to limit, the invention.

Example I

As an example, one of the grids described above can be used in running a cell-based assay, for example, ERK MAPK activation assay available from the Cellomics High Contect Screening division of Thermo Scientific (Product No. K0100071). Below is a standard protocol available from the supplier (i.e., Thermo Scientific) for running the assay at 96-well microplate.

When the assay is adapted to a virtual wall plate of 384-feature format the volume of the assay needs to be reduced accordingly. For example, if a DropArray™ 384-well Cell Plate (commercially available from Curiox Biosystems) is employed, the "well" has only a 2 mm diameter glass area for each element. With the help of a removable grid (such as one of the removable grids described above), the process of miniaturization can be simplified.

The key challenge in miniaturization of this assay is the step of adding a stimulating compound such as Phorbol 12-myristate-13-acetate (PMA) into each element containing cells. For example, a 96-well microplate has a cell solution volume of 100 uL. Then, 25 uL of PMA solution is added on top of the existing 100 uL cell solution. In a 384-feature virtual wall plate of 2 mm diameter feature, this means that the cell solution is at the volume of 3 uL and added with another 0.75 uL, leading to the total volume of 3.75 uL. The total volume of 3.75 uL is over the range of the suggested maximum volume, 3 uL, for 2 mm diameter element on the DropArray™ 384-well Cell Plate.

In a preferred example, the assay can be run in the following manner with the help of a removable grid. A standard 384-element virtual wall plate (e.g., a DropArray™ plate from Curiox Biosystems) with 2 mm diameter element is prepared. An inert fluid, namely Perfluorocarbon Rinsing Oil (commercially available from Curiox Biosystems), is added to the plate followed by draining and leaving about 1 mL of Rinsing Oil in the plate. Then a removable grid wet with the Oil is placed in the plate. In this example, the removable grid is made of PTFE and designed with 2 mm diameter through-holes, 2 mm in height, with an additional peripheral wall around the entire block of 6 mm height. The grid may have bottom-oriented offsetting features. For example, the removable grid may have multiple 0.1 mm-0.5 mm high steps around the edge at the bottom, providing a little space between the virtual wall plate and the main frame of the grid. Such steps may facilitate the addition of a reagent into a well, as the pre-existing inert fluid such as Rinsing Oil can escape through the gap between the plate and the grid. The hydrophobic surface of the grid and the plate prevents hydrophilic reagent, from leaking through the gap under optimal dispensing conditions. When the plate and removable grid is in place, the cell solution is dispensed into the through-holes of the grid. The volume of the cell solution and compound solution such as PMA solution is reduced at the exact ratio of 25 times, for example, from 100 uL to 4 uL.

The volume of the cell solution dispensed to the virtual wall plate and grid is 4 uL. Upon completion of the dispensing 10 mL of Rinsing Oil is added into the plate for overnight incubation. On the next day, after draining the oil from the plate, leaving only a thin layer of Oil left, 1 uL of PMA solution (25% volume with respect to the cell solution) is added, leading to a total volume of 5 uL. Then, 10 mL of Rinsing Oil is added for another 3 hour incubation. When the incubation is completed, the removable grid is removed from the plate, and the plate undergoes a whole plate washing process, for example, a wash by DropArray™ Accelerator HT200. Then, the rest of the process is performed by standard DropArray™ process using 3 uL of reagent at each step without the need of a removable grid.
Cell Preparation Information This protocol is optimized for NIH 3T3 cells (American Type Culture Collection, Product No. CRL-1658).

Briefly, NIH 3T3 cells are cultured using DMEM complete media (HyClone) supplemented with 10% fetal calf serum, 100 units/ml penicillin and 100 µg/ml streptomycin. The cells are split when they reach 70-80% confluency (every 3-4 days) at a dilution of 1:3 to 1:5.

For an ERK activation study using a standard 96 well plate with physical walls, the cells are harvested with trypsin-versene mixture (BioWhittaker, Product No. 17-161F), diluted into DMEM Complete Medium, and cell density is determined (e.g., using a haemocytometer or other cell counter). The cell density is adjusted to $5 \times 10^4$ cells/ml in DMEM Complete Medium and 100 µl of the cell suspension is added to each virtual well of an apparatus described herein having 96 wells (i.e., approximately 5,000 cells/well. The apparatus containing the cells is incubated for 18-24 hours at 37° C. in 5% CO2.

It should be noted that for a standard 96 well plate, 100 µl per well volume is used unless indicated otherwise. This protocol requires ~3 hours to perform once compound incubation has been completed.

For this assay, PMA is prepared at a concentration of 500 ng/ml into culture medium. Add 25 µl/well and mix thoroughly. Incubate 30 minutes at 37° C. For an agonist screen, the compound suspected of being an agonist replaces the stimulator (i.e., PMA is the stimulator). For an antagonist screen, add the compound suspected of being an antagonist before adding the stimulator.

Next, culture medium is aspirated and 100 µl pre-warmed Fixation Solution (e.g., 4% formaldehyde in phosphate buffered saline (PBS) prewarmed to room temperature) is added to each well. The plate is incubated in a fume hood at room temperature for 10 minutes. Note that pre-warming the Fixative Solution prior to adding it t the cells is critical to maintaining cell integrity.

Next, the Fixation Solution is aspirated and the plate is washed once with 100 µl of 1× Blocking Buffer (e.g. 10% bovine serum albumin (BSA) in PBS). Next, the Blocking Buffer is aspirated and 100 µl of 1× Permeabilization Buffer (e.g., 0.1% Triton X-100 in PBS) is added. The plate is then incubated for 15 minutes at room temperature.

Next, the Permeabilization Buffer is aspirated and the plate is washed once with 100 µl of 1× Blocking Buffer. After aspirating the blocking buffer, 50 µl of a Primary Antibody Solution is added per well. The plate is then incubated for 1 hour at room temperature.

Next the Primary Antibody Solution is aspirated, and the plate is washed twice with 100 µl of 1× Blocking Buffer and aspirated from the plate. Next, 50 µl of a Secondary Antibody Solution is added to each well. The plate is then incubated at room temperature for 1 hour protected from light. The Secondary Antibody Solution is then aspirated, and the plated washed twice with 100 µl of 1× Blocking Buffer. After aspirating, 200 µl of 1× Wash Buffer is added to each well. Next, the plate is sealed and evaluated on (e.g., on an ArrayScan HCS Reader). The sealed plates can be stored in the dark at 4° C.

In accordance with the invention, the following is an example of running the ELISA test described above using the grid and system of the invention. A Teflon-printed plate is prepared with a pattern of exposing a bare substrate surface of 1 mmdiameter with a distance of 2.25 mm of Teflon-plating (e.g., forming a hydrophobic surface) between the bare (e.g., hydrophilic) elements. The surface of a Teflon-printed plate is covered with ~2 mL of Rinsing Oil (available from Curiox Biosystems) and drained to leave a thin layer of the oil. A removable grid is added to the plate, the grid can be made of either aluminum or polypropylene. The grid has 96 separated compartments with a wall of 0.5-1 mm thickness and can fit inside the plate exactly (e.g., a snug or friction fit). If made of aluminum, it can be coated with hydrophobic polytetrafluoroethylene (PTFE)-like material. Subsequently, a coating antibody solution of ~0.3-0.4 mL is added to each compartment. When the incubation is completed, the grid is removed from the plate, and the plate undergoes a whole-plate washing, where the plate is exposed to a bulk washing buffer, a typically PBS buffer containing 0.05% Tween™ 20, and shaken for a short duration of time. The same procedure of addition and draining of the oil, placement of the grid, addition of a reagent solution, and removal of the grid followed by washing can be repeated as many as necessary. At the step of adding a fluorogenic substrate, the washing is performed as usual by a whole plate method. Then, a solution of a fluorogenic substrate of ~30-40 mL is added as a bulk and quickly drained by pouring out at, for example, 5-30 degree slanted. The solution left in the plate at such tilting is removed by manual pipetting. Upon complete removal of the substrate solution, the plate is left with an array of small drops of the substrate solution at the volume of 0.2-0.5 mL. Rinsing Oil (Curiox Biosystems) is quickly added to the plate and the plate is read by a plate reader or scanner. Such a procedure can be applied to a plate with 384-feature pattern on the surface. In the example of the 384-feature plate, one compartment of 96-well format grid will encompass 4 elements, for example of 2 mm diameter and 4.5 mm pitch (i.e., a distance of 4.5 mm between horizontally or vertically adjacent elements). Thus, if desired, a sample held in the grid can be probed with 4 different capture probes immobilized on the plate features.

In dispensing reagents into the compartments in the grid, the dispensing step can be performed before or after placing the grid. If the dispensing is performed before the placement, then the wells of a grid should be small enough to hold the reagents by capillary action, for given surface energies of a filling fluid and the grid. For example, the grid with a compartment of bigger than 3 mm, it would generally be better to add reagents after the grid is placed on top of a plate. When the compartment is smaller than 3 mm, the addition of the reagents can generally be performed before the grid is placed on top of a plate.

In order to facilitate the fluidics and assays, it may be desirable to treat the inner surface of a well of a grid to present a surface of a particular nature. For example, the surface may be hydrophilic when it is desirable to better hold aqueous reagent in the well. In another example, the surface may expose a non-fouling surface in order to minimize the non-specific adsorption of proteins to the surface during incubation of reagents.

In particular, a hydrophilic surface may facilitate the addition of fluid, usually aqueous solution, into the through-holes of a grid as such surface will naturally 'wick' aqueous solution.

A grid for array-in-array applications can be added and removed freely to a plate made with flat bottom slide. When the plate needs to be washed, the grid can be conveniently removed from the plate. Then, the plate is washed by a bulk washing method instead of well-by-well washing method.

Example II

Suspension cells (e.g., suspension cell lines or blood cells) by nature are designed to stay in suspension and exhibit little adherence to a physical substrate in contrast to adherent cells that show relatively stronger adhesion to a physical substrate. Due to the non-adherent nature of suspension cells, it is challenging to wash the cells, a step that is typically required for common and popular methods of studying and such analyzing cells. During a washing process, the existing fluidic reagent containing cells is replaced with another fluidic reagent. In such process, cells are often exposed to a neutral fluidic reagent multiple times by undergoing the step of addition, centrifuging and decanting, before the addition of another fluidic reagent. The reason for washing with the neutral fluidic reagent is to ensure the complete removal of the existing fluidic reagent before the addition of another fluidic reagent. Unlike handling of adherent cells, which stay adherent to a physical substrate and facilitate the removal of an existing fluidic reagent co-present with cells without loss of cells, suspension cells can be easily lost during the washing process.

In the current practices, suspension cells usually undergo centrifuging before decanting of a co-present fluidic reagent. Centrifuging helps the cells to clump together and reduces the loss of cells during decanting. The requirement of centrifuging at every step of decanting makes the whole process of cell analysis extremely tedious, laborious, and automation-unfriendly. Furthermore, even after the centrifuge step, the clumped cells are still labile and easily come off during the liquid handling step.

A simple modification of a DropArray™ plate or a similar flat plate with or without extremely shallow wells can enable the handling of suspension cells in the same manner as that of adherent cells. A DropArray™ plate carries a flat slide at the bottom with hydrophobic and hydrophilic pattern, where hydrophilic features are employed in the similar capacity of a well in a conventional microtiter plate. For the intended application with suspension cells, if the cells are laid as a single layer, the flat slide of a DropArray™ plate or a similar flat plate may be employed to run a washing process in the same manner as for adherent cells. However, when the cells are laid as multiple layers on the surface of a plate, the flat slide of a DropArray™ plate or a similar plate may be modified to introduce a little step at the contact between hydrophobic and hydrophilic area (i.e., create a "well" sided by the hydrophilic or hydrophobic through-holes and bottomed by the hydrophilic element). Specifically, the hydrophilic elements are located slightly below the plane of overlay surface.

Figure 11:
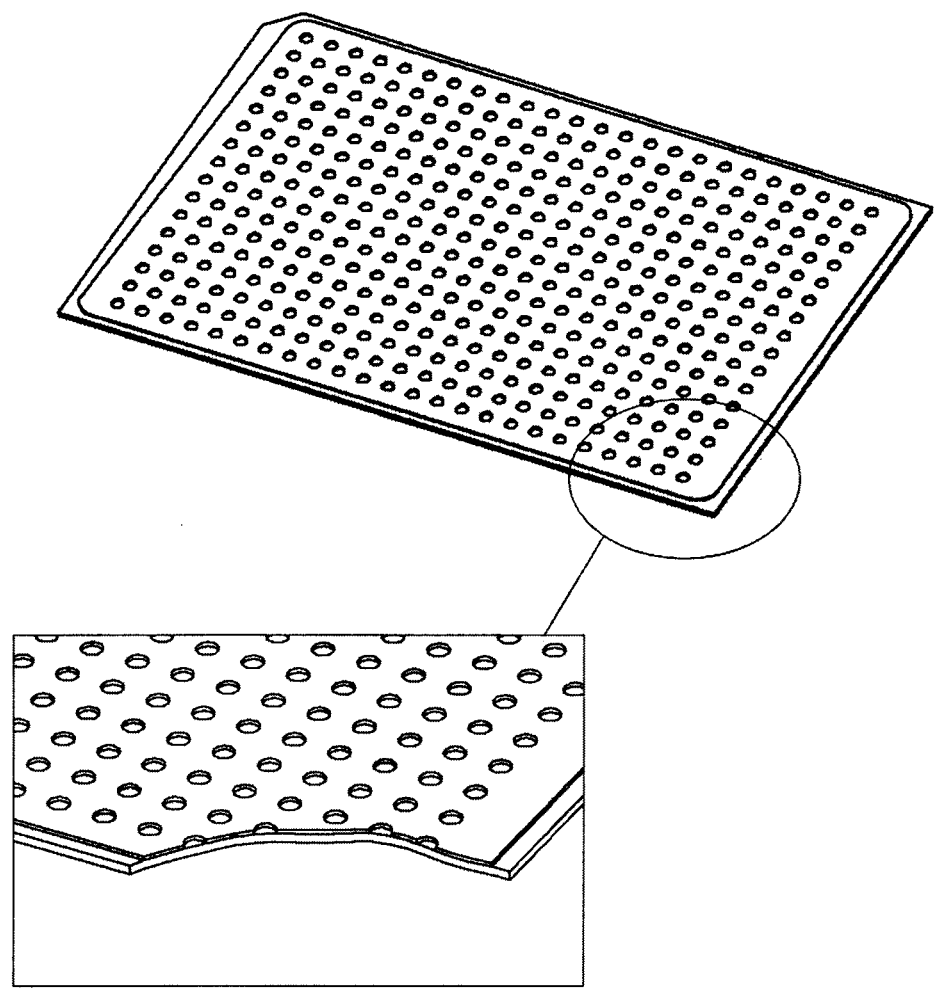
FIG. 11 is a schematic representation of a non-limiting apparatus of the invention, where the hydrophobic overlay is raised a height of at least 5% of the diameter of a hydrophilic element above the hydrophilic elements. In the lower panel of FIG. 11, a close-up view of a cross-section of the non-limiting apparatus is depicted.

FIG. 11 shows an example of a flat plate to be assembled as an apparatus (e.g., a modification of a DropArray™ plate) for the application of suspension cell assay as a single layer. In the plate, the hydrophilic elements slightly recessed from the hydrophobic overlay of the slide. The degree of recess may vary depending on the diameter of hydrophilic feature and stringency of washing required. For example, the recession of 0.1-2 mm may be desirable for the diameter of 2 mm of hydrophilic feature. The sidewall of the hydrophobic overlay (i.e., the exposed hydrophobic region inside the recess) may, in some embodiments, present the same hydrophobic surface at the surface of the hydrophobic overlay (i.e., the surface that will touch the bottom of the grid when the grid is inserted), but this is not always required. In the fabrication of a plate, for example, a transparent slide is made of a glass or transparent polymeric material such as cyclic olefin copolymer (COC), polystyrene or polycarbonate. The hydrophobic overlay material may be made of polytetrafluoroethylene (PTFE). The hydrophobic material can be either attached to the transparent slide by non-cytotoxic adhesive or embedded by a process such as insert molding. When the hydrophobic material is attached, the side of the hydrophobic material should be treated in a way that a glue or adhesive can bind, as PTFE or similarly hydrophobic material generally shows poor adhesion. As for the depth of the recess and the diameter of a hydrophilic element, the depth of the recess is expected to increase as the diameter of the hydrophilic element increases. The surface of a hydrophilic element may be treated by, for example, gas plasma, or coated with a film such as a protein and/or polypeptides such as fibronectin or polylysine in order to improve the adhesion of the cells onto the surface of the hydrophilic element.

The presence of the recess around hydrophilic features is believed to reduce the shear force from the fluidic movement of a washing solution created from the shaking of a plate and impacting the cells sitting on the surface of hydrophilic features. In the process of the present embodiment, a plate is assembled with a cover to create a water-tight reservoir. Then, a washing solution is added into the reservoir followed by shaking or other means to create the flow of the washing solution. The flow of the solution helps to dilute reagents present on each hydrophilic feature, which later is decanted from the reservoir.

It is desirable to fabricate the plate in a way that the flat slide of the plate presents both hydrophilic and hydrophobic surfaces on the same plane. Such configuration maximizes the mixing of the reagent with a washing solution. However, the materials such as proteins and cells present on the hydrophilic surfaces experience relatively significant shear force by the movement of the fluid. For proteins in ELISA tests and adherent cells in adherent-cell-based assays, the washing condition is optimized in a way that the direct shear force does not damage the outcome.

When a flat slide of a plate is built with a slight recess, the shear force applied on those materials on hydrophilic surface is substantially reduced while the mixing of the reagent in hydrophilic feature with a washing solution is reasonably satisfactory although the degree of mixing is not as strong as that of a flat plate. Accordingly, the embodiment of the present invention features a recess depth that is sufficient small to allow washing of the features yet sufficiently large to discourage displacement of suspension cells.

FIG. 11 shows an example of an apparatus of the invention (i.e., flat slide patterned with hydrophobic and hydrophilic area and a surrounding wall), where hydrophilic area is slightly recessed from the plane of hydrophobic area.

Figure 12:
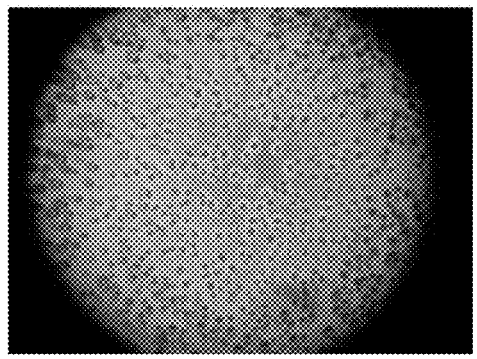
FIG. 12 are a series of photographs of sp2 cells on a "recess" DropArray™ plate, incubated overnight followed by a series of washing step performed by DropArray™ Accelerator LT100. The left panel shows a well with cells before washing after overnight incubation. The three panels on the right show the same well after $1^{st}$, $2^{nd}$ and $6^{th}$ wash.
Figure 12:
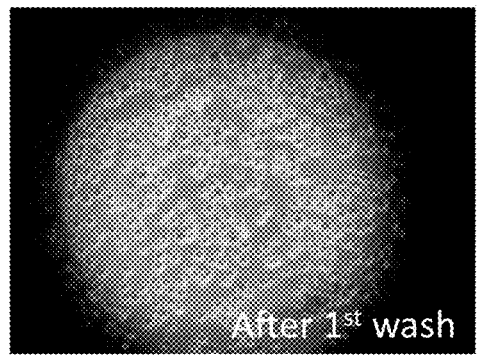
Figure 12:
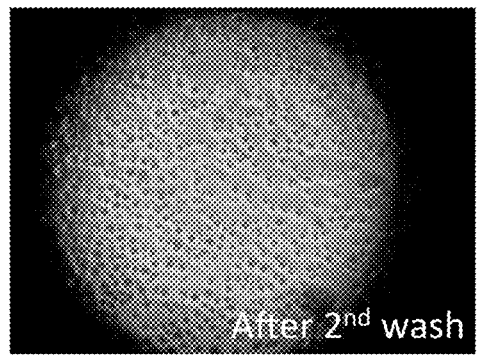
Figure 12:
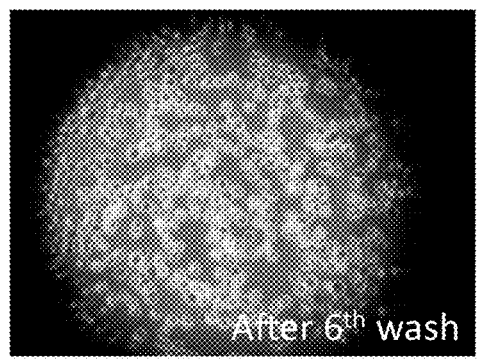

The configuration of DropArray™ plate exposing slightly recessed hydrophilic features was successfully tested and demonstrated minimal loss of suspension cells upon extensive washing of the plate. FIG. 12 shows an example of washing test performed with a suspension cell line, sp2 cell line. In this test, sp2 cells were dispensed onto a 48-well DropArray™ plate in a volume of 3 uL per well. The DropArray™ plate was coated with Poly-L-Lysine to enhance the binding of the cells onto the hydrophilic surface. After overnight incubation at 37° C., the plate underwent typical cell washing process in DropArray™ Accelerator LT100. In the process, the plate is assembled with a cover, followed by introduction of 45 mL 1× phosphate buffered saline (PBS) buffer and shaking at 40 rpm for 10-20 seconds.

The washing was repeated while cells on the plate were observed and imaged between the washing steps. The left panel in FIG. 12 shows a well with ps2 cells after overnight incubation, before washing. The second, third and bottom panel shows a photograph taken from a same well after $1^{st}$, $2^{nd}$ and $6^{th}$ washes. After $6^{th}$ wash, it was observed that a significant portion of cells were dying, presumably due to the washing buffer used, 1×PBS affecting the integrity of cells. Still, the loss of cells was relatively insignificant, indicating gentleness of the washing on the cells.

In the example of washing suspension cells of multilayers, the plate may be modified to contain 2 mm diameter of hydrophilic elements with, for example, 1-2 mm depth (i.e., the height of the overlay is 1-2 mm). Furthermore, the washing may be modified to reduce the stress by fluidics. For example, the wash buffer is introduced and drained at a lower flow rate, say 50% of the conventional flow rate and the shaking is reduced to 0-20 rpm. Instead of the reduced or the absence of shaking, the plate may include a resting period of, for example, 20-60 seconds at each washing step in order to induce natural diffusion of the reagent to the bulk wash buffer. With the increased depth and gentler fluidics, the hydrophilic element of 2 mm diameter may be able to retain more than 50% of cell numbers of, for example, Jurkat T cells at the density of 3000 cells per element, after 3 times repeated washing.

Example III

In this example, the Cell Titer96® Aqueous Non-Radioactive Cell Proliferation Assay (sold by Promega Corp., Madiscon, Wis., USA) is miniaturized using the grid and system of the invention.

The protocol for the Cell Titer96® Aqueous Non-Radioactive Cell Proliferation Assay is available in Promega's Technical Bulletin for Products G5421, G5430, G5440, G1111, and G1112 (Rev. 5/09; Part#TB169 from Promega Corp.).

As described in Example I, adherent cells are grown on a 384-element DropArray™ plate. The adherent cells used in this example are the MCF7 human breast cancer cells (commercially available from American Type Culture Collection; Manassas, Va., USA). In this experiment, the amount of tumor necrosis factor alpha (TNFa) need to inhibit cell growth by 90% was determined by tittering the amount of TNFa added to the cells.

The cells are grown in Eagle's minimum Essential Medium (ATCC Catalog No. 30-2003) with 0.01 mg/ml bovine insulin and 10% fetal bovine serum ("culture media"). 2 ul droplets of culture media containing MCF7 cells are pipetted onto the elements of an apparatus (in this case, a 384 element Droparray™ plate), and the plate is incubated for 24 hours at 37° C. in 5° C. $CO_2$.

Ninety-five different concentrations of TNFa are made in culture media. A grid comprising 96 through-holes is inserted into the apparatus such that four elements (and four different cell populations) are within each grid. A standard pipet is then used to add 4 ul of each of the 95 TNFa concentrations to each through-hole. A final 4 ul of culture media with no TNFa is added to the $96^{th}$ through-hole of the grid. After the 4 ul drops are delivered, the plate is gently tilted manually until the 4 ul drops are dispersed into each of the 4 elements within the through-hole. The plate is then returned to incubation for 24 hours at 37° C. in 5° C. $CO_2$. During incubation, the grid is left on the apparatus.

After incubation, the grid is removed and the plate washed in a DropArray™ Accelerator LT100 (commercially available from Curiox Biosystems) as described above. MTS Solution and the PMS solution from the CellTiter96 plate are prepared as described in Promega's Technical Bulletin.

A different grid, comprising 384 through-holes where the through-holes have a slightly larger diameter than the 2 mm diameter of the elements of the DropArray™ plate is next inserted into the plate. 5 ul of the MTS/PMS solution is added into each through-hole of the grid. The plate (with inserted grid) is next incubated for 4 hours at 37° C. in 5° C. $CO_2$. The plate is then removed from the incubator and absorbance read immediately at 490 nm using a standard ELISA plate reader configured for 384 wells.

Using the absorbance values from the four cell populations treated with the same amount of TNFa, the ED50 value of TNFa on MCF7 cells can be readily determined with the degrees of confidence obtained from this study that used few reagents and few cells.

Example IV

In this example, an embodiment of the plate depicted in FIG. 11 will be employed to assess which height is useful in retaining two commonly used suspension cells. The optimal height will vary depending upon the cell type and specific characteristic of that cell (e.g., mass, diameter, and reaction assay being performed). The following two suspension cells (all commercially available from the ATCC (Manassas, Va., USA)) will be used: human Jurkat T cells (ATCC No. TIB-152) and human Daudi B cells (ATCC No. CCL-213).

In this example, three different 384 element apparatuses based on the apparatus depicted in FIG. 11 are employed. All have 384 elements of 2 mm diameter each. The first apparatus has an overlay height of 0.5 mm over the surface of the elements. The second has a height of 1 mm. And, the third has a height of 2 mm.

Different numbers of Daudi and Jurkat cells are plated onto each of the apparatuses, where the same number of each cell type is plated onto elements in the same location of each of the four apparatuses. Since both Daudi and Jurkat cells express CD5 antigen at their cell surface, a detectably labeled anti-human CD5 antibody is added to each well (e.g., the AlexFluor 700-labeled anti-human CD5 antibody sold as Catalog No. 561159 by BD Biosciences, San Diego, Calif., USA). After washing the apparatuses using the cell washing process in the DropArray™ Accelerator HT200 (Curiox Biosystems, Signapore), the amount of fluorescence is determined using a standard ELISA plate reader and the cells are counted (e.g., using a haemocytometer or other standard cell counting technique).

In this manner, the optimal apparatus (i.e., the optimal height of the overlay) for each cell type can be determined that retains the greatest amount of cells and the lowest amount of background (i.e., unbound AlexFluor anti-CD5 antibody). Furthermore, the washing may be modified to reduce the stress by fluidics. For example, the wash buffer is introduced and drained at a lower flow rate, say 50% of the conventional flow rate and the shaking is reduced to 0-20 rpm. Instead of the reduced or the absence of shaking, the plate may include a resting period of, for example, 20-60 seconds at each washing step in order to induce natural diffusion of the reagent to the bulk wash buffer. With the increased depth and gentler fluidics, the hydrophilic element of 2 mm diameter may be able to retain more than 50% of cell numbers of, for example, Jurkat cells or Daudi cells at the density of 3000 cells per element, after 3 times repeated washing.

While the invention has been described with particular reference to the illustrated embodiments, it will be understood that numerous modifications thereto will appear to those skilled in the art. Accordingly, the above description, the following claims, and accompanying drawings should be taken as illustrative of the invention and not in a limiting sense.

What is claimed is:

1. An apparatus for improving retention of non-adherent cells on a plate, the apparatus comprising:
   the plate comprising a number of elements having a first surface energy arranged in an array with an overlay, on the plate, having a second surface energy, the first surface energy resulting in a hydrophilic surface and the second surface energy resulting in a hydrophobic surface, wherein:
      a diameter of the elements is at least 1 mm; and
      a height of the overlay having the second surface energy, which results in a hydrophobic surface, is between 5% and 100% of the diameter of the elements;
   a wall circumferential to the plate; and
   a removable grid insertable into the apparatus to be positioned over the plate and within the wall of the apparatus, the grid comprising dividers enclosing a number of through-holes, said through-holes spaced in the grid to allow alignment of the through-holes of the grid over the elements in the plate when the grid is inserted into the apparatus, wherein said dividers of the grid inserted into the apparatus form sides of wells bottomed by the plate and at least one element on said plate, the grid has a surface energy that results in a hydrophobic surface, and the grid is distinct and separate from the overlay and the wall.

2. The apparatus of claim 1, wherein the apparatus further comprises a positioning structure adjacent to the interior of the wall so as to guide alignment of the through-holes of the grid over the elements when the grid is inserted into the apparatus.

3. The apparatus of claim 1, wherein the number of through-holes in the grid is the same as the number of elements in the plate.

4. The apparatus of claim 1, wherein the number of though-holes in the grid is smaller than the number of elements in the plate.

5. The apparatus of claim 4, wherein each through-hole is aligned over multiple elements in the plate.

6. The apparatus of claim 1, wherein the grid further comprises baffles on the surface of the grid that touches the plate when the grid is inserted into the apparatus.

7. The apparatus of claim 1, wherein the grid has the second surface energy.

8. The apparatus of claim 1, wherein the grid further comprises at least one structure on the surface of the grid that does not touch the plate when the grid is inserted into the apparatus, said structure sized for a user to grab the grid and insert or remove the grid from the apparatus.

9. The apparatus of claim 1, wherein the grid further comprises a reservoir encompassing at least one through-hole of the grid, said reservoir on the surface of the grid that does not touch the plate when the grid is inserted into the apparatus.

10. The apparatus of claim 1, wherein the dividers of the grid and the wall of the apparatus are of the same height.

11. The apparatus of claim 1, wherein the dividers of the grid are of a height that is higher than the height of the wall of the apparatus.

12. The apparatus of claim 1, wherein the grid further comprises a lid perpendicular to the dividers of the grid attached to the surface of the grid that does not touch the plate when the grid is inserted into the apparatus, wherein the lid covers all of the through-holes of the grid.

13. The apparatus of claim 12, wherein the lid further comprises sides perpendicular to said lid, said sides parallel to and shorter than the dividers of the grid.

14. The apparatus of claim 13, wherein the grid further comprises baffles between the dividers and the lid.

15. The apparatus of claim 1, wherein the height of the overlay over the elements is between 10% and 80% of the diameter of the elements.

16. The apparatus of claim 1, wherein the height of the overlay over the elements is between 20% and 50% of the diameter of the elements.

17. The apparatus of claim 1, wherein the dividers are aligned directly over the hydrophobic surface the overlay having the second surface energy resulting in the hydrophobic surface when the grid is inserted into the apparatus.

18. The apparatus of claim 1, wherein the wall circumferential to the plate defines a reservoir and the apparatus includes an oil within the reservoir.

19. The apparatus of claim 18, wherein the removable grid has a weight that prevents flotation of the removable grid on the oil within the reservoir.

20. The apparatus of claim 1, wherein the diameter of the element is at least 2 mm.

21. The apparatus of claim 1, wherein the overlay is made of polytetrafluoroethylene.

22. A method for performing multiple reactions, comprising:
   (a) providing (i) an apparatus for improving retention of non-adherent cells on a plate, the apparatus comprising the plate comprising a number of elements having a first surface energy arranged in an array with an overlay, on the plate, having a second surface energy, the first surface energy resulting in a hydrophilic surface and the second surface energy resulting in a hydrophobic surface, wherein a diameter of the elements is at least 1 mm and a height of the overlay having the second surface energy, which results in a hydrophobic surface, is between 5% and 100% of the diameter of the elements; (ii) a wall circumferential to the plate; and (iii) a removable grid insertable into the apparatus to be positioned over the plate and within the wall of the apparatus, the grid comprising dividers enclosing a number of through-holes, said through-holes spaced in the grid to allow alignment of the through-holes of the grid over the elements in the plate when the grid is inserted into the apparatus, wherein said dividers of said grid inserted into the apparatus form sides of wells bottomed by the plate and at least one element on said plate, the grid has a surface energy that results in a hydrophobic surface, and the grid is distinct and separate from the overlay and the wall;

(b) adding a first reagent-containing liquid through the through-holes of the grid under conditions where the first reagent in the liquid adheres to the elements on the plate;
(c) adding rinsing oil to said plate in an amount necessary to cover said plate;
(d) draining excess rinsing oil from the plate resulting from step (c);
(e) adding a liquid through the through-holes of the grid, said liquid containing a second reagent suspected of reacting with the first reagent;
(f) removing the grid from the apparatus;
(g) washing the apparatus; and
(h) detecting reaction of the second reagent with the first reagent.

23. The method of claim 22, wherein the first reagent is a cell.

24. The method of claim 23, wherein the cell is selected from the group consisting of an adherent cell, a non-adherent cell, and a permeabilized cell.

25. The method of claim 23, wherein the second reagent is selected from the group consisting of an agonist or an antagonist.

26. The method of claim 22, wherein the first reagent is a binding agent.

27. The method of claim 26, wherein the binding agent is selected from the group consisting of a single-stranded nucleic acid molecule, an antibody, and a ligand.

28. The method of claim 22 further comprising inserting the grid into the apparatus following step (g).

29. The method of claim 22, wherein step (h) is performed using a third reagent.

30. The method of claim 29, wherein the third reagent is detectably labeled.

* * * * *